United States Patent
Roh et al.

(10) Patent No.: US 9,458,120 B2
(45) Date of Patent: Oct. 4, 2016

(54) PHENOXYPROPANOL DERIVATIVE AND PHARMACEUTICAL COMPOSITION INCLUDING THE SAME

(71) Applicant: KOREA INSTITUTE OF SCIENCE AND TECHNOLOGY, Seoul (KR)

(72) Inventors: Eun-Joo Roh, Seoul (KR); Kye-Jung Shin, Seoul (KR); Changjoon Justin Lee, Seoul (KR); Soo Jin Oh, Seoul (KR); Jung-Eun Park, Seoul (KR); Jeong Eun Yang, Suwon-si (KR); Eun Mi Hwang, Jinju-si (KR); Dong Ho Woo, Seoul (KR); Soon-Hyouk Lee, Daejeon (KR); Dong-Gyu Kim, Gyeongsangnam-do (KR); Hee-jung Chun, Seoul (KR); Wan-Keun Ji, Seoul (KR); Yun-Soo Na, Gyeonggi-do (KR)

(73) Assignee: KORBA INSTITUTE OF SCIENCE AND TECHNOLOGY, Seoul (KR)

( * ) Notice: Subject to any disclaimer, the term of this patent is extended or adjusted under 35 U.S.C. 154(b) by 111 days.

(21) Appl. No.: 14/361,844

(22) PCT Filed: Nov. 30, 2012

(86) PCT No.: PCT/KR2012/010322
§ 371 (c)(1),
(2) Date: Oct. 16, 2014

(87) PCT Pub. No.: WO2013/081420
PCT Pub. Date: Jun. 6, 2013

(65) Prior Publication Data
US 2015/0166496 A1    Jun. 18, 2015

(30) Foreign Application Priority Data

Nov. 30, 2011    (KR) .................. 10-2011-0127053

(51) Int. Cl.
| | |
|---|---|
| *C07D 295/15* | (2006.01) |
| *A61K 31/496* | (2006.01) |
| *C07D 295/088* | (2006.01) |
| *C07D 231/40* | (2006.01) |
| *C07D 211/22* | (2006.01) |
| *C07D 211/38* | (2006.01) |
| *C07D 211/52* | (2006.01) |
| *C07D 211/58* | (2006.01) |
| *C07D 233/64* | (2006.01) |
| *C12N 5/071* | (2010.01) |
| *C07D 401/04* | (2006.01) |
| *C07D 403/06* | (2006.01) |
| *C07D 413/04* | (2006.01) |
| *A61K 31/495* | (2006.01) |
| *A61K 31/454* | (2006.01) |
| *A61K 31/4545* | (2006.01) |
| *A61K 31/5377* | (2006.01) |

(52) U.S. Cl.
CPC ........... *C07D 295/15* (2013.01); *C07D 211/22* (2013.01); *C07D 211/38* (2013.01); *C07D 211/52* (2013.01); *C07D 211/58* (2013.01); *C07D 231/40* (2013.01); *C07D 233/64* (2013.01); *C07D 295/088* (2013.01); *C12N 5/0686* (2013.01); *C12N 2501/999* (2013.01)

(58) Field of Classification Search
None
See application file for complete search history.

(56) References Cited

U.S. PATENT DOCUMENTS

| | | |
|---|---|---|
| 5,906,988 A | 5/1999 | Dow et al. |
| 7,125,876 B2 | 10/2006 | Elzein et al. |
| 7,407,960 B2 | 8/2008 | Elzein et al. |
| 7,642,262 B2 | 1/2010 | Annoura et al. |

FOREIGN PATENT DOCUMENTS

| | | |
|---|---|---|
| EP | 0719558 | 7/1996 |
| WO | 2004/052887 | 6/2004 |

OTHER PUBLICATIONS

CA Registry No. 1010941-29-3, entered into the Registry File on Mar. 30, 2008 and 1010620-42-4, entered into the Registry File on Mar. 28, 2008 supplied by Ambinter.*
Arnoult et al., "Activation of mouse sperm T-type $Ca^{2+}$ channels by adhesion to the egg zona pellucid" Proc. Natl. Acad. Sci. USA, vol. 93, Nov. 1996, pp. 13004-13009.

(Continued)

*Primary Examiner* — Emily Bernhardt
(74) *Attorney, Agent, or Firm* — Goldilocks Zone IP Law

(57) ABSTRACT

The present invention relates to a novel phenoxypropanol derivative, represented by the structure of Chemical Formula I, and a racemate thereof, a pharmaceutically acceptable salt thereof, a solvate thereof and a hydrate thereof,

[Chemical Formula I]

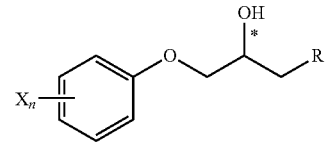

wherein * represents an (R)-form or an (S)-form, X is selected from the group consisting of hydrogen, halogen and substituted or unsubstituted straight or branched alkyl having 1 to 4 carbon atoms, and n represents the number of X and an integer of 1 to 5, wherein at least a hydrogen is substituted with halogen in the substituted linear or branched alkyl having 1 to 4 carbon atoms. The derivative can be used for blocking T-type calcium channel and/or TREK channel, and for preventing and/or treating T-type calcium channel- and/or TREK channel-associated diseases.

3 Claims, No Drawings

(56) References Cited

OTHER PUBLICATIONS

Clozel et al., "The Structurally Novel $Ca^{2+}$Channel Blocker Ro 40/5967, Which Binds to the [$^3$H] Desmethoxyverapamil Receptor, Is Devoid of the Negative Inotropic Effects of Verapamil in Normal and Failing Rat Hearts", Cardiovascular Drugs and Therapy 4, 1990, pp. 731-736.

Felix et al., "ZD77288 inhibits low-threshold $Ca^{2+}$channel activity and regulates sperm function", Biochemical and Biophysical Research Communications 311, 2003, pp. 187-192.

Hefti et al., "Antihypertensive Properties of the Novel Calcium Antagonist (1S,2S)-2-[2-[[3-(2-Benzimidazolyl)propyl]methylamino]ethyl}-6-fluoro-1,2,3,4-tetrahydro-1-isopropyl-2-naphthyl Methoxyacetate Dihydrochloride in Rat Models of Hypertension", Arzneimittelforschung, 40, 1900, pp. 417-421.

Huguenard, "Low-Threshold Calcium Currents in Central Nervous System Neurons", Annu. Rev. Physiol., vol. 58, 1996, pp. 329-348.

Ikeda et al., "Synaptic Plasticity in Spinal Lamina I Projection Neurons That Mediate Hyperalgesia", Science 299, 2003, pp. 1237-1240.

Kemp et al., "Regulation of recombinant human brain tandem P domain $K^+$ channels by hypoxia: a role for $O_2$ in the control of neuronal excitability?", Neuroscience Review Series, J. Cell. Mol. Med. vol. 8, No. 1, 2004, pp. 38-44.

Llinás et al., "Electrophysiology of Mammalian Inferior Olivary Neurones in Vitro. Different Types of Voltage-Dependent Ionic Conductances", J. Physiol., 315, 1981, pp. 549-567.

Miller et al., Polymodal regulation of hTREK1 by pH, arachidonic acid, and hypoxia: physiological impact in acidosis and alkalosis, Am J Physiol Cell Physiol 286, 2004, pp. C272-C282.

Perez-Reyes et al., "Molecular characterization of a neuronal low-voltage-activated T-type calcium channel", letters to nature, vol. 391, Feb. 1998, pp. 896-900.

Rossier et al., "Distinct Functions of T- and L-Type Calcium Channels during Activation of Bovine Adrenal Glomerulosa Cells", Endocrinology, vol. 137, No. 11, 1996, pp. 4817-4826.

Schaible et al., "The role of high-threshold calcium channels in spinal neuron hyperexcitability induced by knee inflammation", Progress in Brain Research, vol. 129, 2000, pp. 173-190.

Self et al., "Stroke-Prone SHR Vascular Muscle $Ca^{2+}$ Current Amplitudes Correlate with Lethal Increases in Blood Pressure", J Vasc Res, 31, 1994, pp. 359-366.

Kim et al., "Thalamic Control of Visceral Nociception Mediated by T-Type $Ca^{2+}$ Channels", Science 302, 2003, 5 pp.

Talley et al., "Differential Distribution of Three Members of a Gene Family Encoding Low Voltage-Activated (T-Type) Calcium Channels", The Journal of Neuroscience, 19(6), 1999, pp. 1985-1911.

Todorovic et al., "Redox Modulation of T-Type Calcium Channels in Rat Peripheral Nociceptors", Neuron, vol. 31, Jul. 2001, pp. 75-85.

Tsakiridou et al., "Selective Increase in T-Type Calcium Conductance of Reticular Thalamic Neurons in a Rat Model of Absence Epilepsy", The Journal of Neuroscience, 15(4), Apr. 1995, pp. 3110-3117.

Tsien et al., "Multiple types of neuronal calcium channels and their selective modulation", TINS, vol. 11, No. 10, 1988, pp. 431-438.

Viana et al., "Mibefradil (Ro 40-5967) blocks multiple types of voltage-gated calcium channels in cultured rat spinal motoneurones", Cell Calcium, 22(4), 1997, pp. 299-311.

Zhou et al., "T-Type Calcium Current in Latent Pacemaker Cells Isolated from Cat Right Atrium", J Mol Cell Cardiol, 26, 1994, 1211-1219.

Xu et al., "Alterations in the expression of lipid and mechano-gated two-pore domain potassium channel genes in rat brain following chronic cerebral ischemia", Molecular Brain Research 120, 2004, pp. 205-209.

Volodhyna et al., "TREK-1 Is a Novel Molecular Target in Prostate Cancer", Cancer Research, 2008, pp. 1197-1203.

Gordon et al., "TREKing toward new antidepressants", Nature Neuroscience, vol. 9, No. 9, Sep. 2006, pp. 1081-1083.

Nuss et al., "T-type $Ca^{2+}$ current is expressed in hypertrophied adult feline left ventricular myocytes.", Circulation Research, Journal of the American Heart Association, 1993, pp. 777-782.

McCormick et al., "Functional Implications of Burst Firing and Single Spike Activity in Lateral Geniculate Relay Neurons", Neuroscience vol. 39, No. 1, 1990, pp. 103-113.

Heurteaux et al., "Deletion of the background potassium channel TREK-1 results in a depression-resistant phenotype", Nature Neuroscience, vol. 9, No. 9, Sep. 2006, pp. 1134-1141.

\* cited by examiner

PHENOXYPROPANOL DERIVATIVE AND PHARMACEUTICAL COMPOSITION INCLUDING THE SAME

CROSS-REFERENCE TO RELATED APPLICATION

This application claims priority to and the benefit of Korean patent application number 10-2011-0127053, filed in the Korea Intellectual Property Office on Nov. 30, 2011, the entire contents of which are incorporated herein by reference.

TECHNICAL FIELD

The present invention relates to a novel phenoxypropanol derivative, use thereof for blocking T-type calcium channel and/or TREK channel, and use thereof for preventing and/or treating T-type calcium channel- and/or TREK channel-associated diseases.

BACKGROUND ART

Calcium in nerve cells plays an important role in transferring signals between the nerve cells. There are several channels for calcium. However, when a terminal stimulus is transferred thereto, a voltage-dependent calcium channel (voltage-dependent $Ca^{2+}$ channel) works primarily. That is, the voltage-dependent calcium channel as a membrane protein regulates various intracellular functions such as muscle contraction, neurogenesis, synapse plasticity, secretion of neurotransmitter and hormone, gene expression, etc. by controlling an inflow of calcium ion from a cell exterior.

The voltage-dependent calcium channel can be functionally classified depending on its biophysical property: a low voltage-activated $Ca^{2+}$ channel (hereinafter referred to as "LVA"), which is activated at lower voltage; and a high voltage-activated $Ca^{2+}$ channel (hereinafter referred to as "HVA"), which is activated at higher voltage. The HVA calcium channel is subdivided into L-, P/Q-, N- and R-types depending on a pharmacological property of the current induced thereby. The LVA calcium channel is characterized by small conductivity being very quickly activated and inactivated. Thus, it is commonly called T (transient)-type calcium channel (Tsien, R. W. et al., Trends Neurosci. 1988, 11, 431-438).

It has been reported that the T-type calcium channel is involved in bursting firing of nerve cells (Huguenard, J. R. et al., Annu. Rev. Physiol. 1996, 58, 329-348), pacemaker activity of the heart (Zhou, Z et al., J. Mol. Cell. Cardiol. 1994, 26, 1211-1219), secretion of the hormone aldosterone (Rossier, M. F. et al., Endocrinology 1996, 137, 4817-4826), and fertilization (Arnoult, C. et al., Proc. Natl. Acad. Sci. 1996, 93, 13004-13009). In addition, the T-type calcium channel may become over-expressed due to genetic or environmental causes, leading to diseases such as epilepsy (Tsakiridou, E. et al., J. Neurosci. 1995, 15, 3110-3117), high blood pressure (Self, D. A. et al. J. Vacs. Res. 1994, 31, 359-366), ventricular hypertrophy (Nuss, H. B. et al., Circ. Res. 1995, 73, 777-7825), pain (Shin, H. S. et al., Science 2003, 302, 117-119), and angina pectoris (Van der Vring, J. A. et al., Am. J. Ther. 1999, 6, 229-233).

Recently, it has been also reported that the T-type calcium channel is involved in pain relief (Ikeda, H. et al., Science 2003, 299, 1237-1240). The HVA calcium channel is evenly expressed from the peripheral sensory cells to the central nervous system, and is well known to play an important role in transmission of the sense of pain and reflection. The inhibitors against these channels are already commercially available as various anodynes (Schaible, Prog. Brain Res., 2000, 129:173-190).

However, it is not yet clearly understood how the LVA calcium channel that generates the T-type calcium current can regulate pain. The reason why the T-type calcium current is categorized as one of the functions of the LVA calcium channel is that when the excitability of nerve cells lowers, the calcium current are generated so that the excitability increases again (Llinas, J. Physiol (Lond), 1981, 315:549-567; McCormick, Neuroscience, 1990, 39:103-113). Thus, the nerve cells excited by the T-type calcium channel have the property of burst firings and induce a type of excitability different from tonic firings (Llinas, J. Physiol (Lond), 1981, 315:549-567).

The channel protein of the T-type calcium channel is encoded by three different genes, which are referred to as alpha($\alpha$)1G, $\alpha$1H and $\alpha$1I, respectively (Perez-Reyes, Nature, 1998, 391:896-900). It is known that the $\alpha$1G and $\alpha$1H T-type calcium channels are expressed in the back of the spinal cord, and that the $\alpha$1G is expressed in thalamo-cortical relay neurons (Talley, J. Neurosci., 1999, 19:1895-1911), and that is identical with the delivery path of the visceral pain. Recently, it has been proved in an experiment using a T-type calcium current inhibitor, mibefradil (registered trademark: Posicor, Hoffman La Roche Ltd.) that the function of the T-type calcium current in the peripheral nerves is related to hyperalgesic reaction against thermostimuli or mechanical stimuli by reducing agents (Todorovic, Neuron, 2001, 31:75-85), however, it has not yet been found which T-type calcium channel is related. Mibefradil was initially known for lowering blood pressure (Clozel, Cardiovasc Drugs Ther., 1990, 4:731-736; Hefti, Arzneimittelforschung, 1990, 40:417-421), and was reported to have a suppression effect on several calcium channels including T-type calcium channel (Viana, Cell Calcium, 1997, 22:299-311). Recently, it has been reported that Mibetradil has the most selective suppression effect on T-type calcium channels.

However, there were no effective T-type calcium channel blockers except for Mibefradil and ZD7288 (Felix, R. et al., Biochem. Biophys. Res. Commun. 2003, 311, 187-192). Accordingly, by developing a selective T-type calcium channel blocker, it may be possible to develop an epochal treating agent for cardiovascular diseases such as high blood pressure, angina pectoris, heart failure and arrhythmia, as well as pain-related diseases.

TECHNICAL PROBLEM

In the present invention, a new substance which is a blocker selectively acting on T-type calcium channel and/or TREK (TWIK-related $K^+$) channel is developed as an alternative to Mibefradil and ZD7288, and therefore, it is intended to provide use thereof as a T-type calcium channel blocker and/or a TREK channel blocker.

Accordingly, an object of the present invention is to provide a novel phenoxypropanol derivative.

Another object of the present invention is to provide a selective blocker for T-type calcium channel and/or TREK channel, including the phenoxypropanol derivative as an active ingredient.

Still another object of the present invention is to provide use of the blocker including the propanol derivative as an active ingredient for preventing, improving, and/or treating T-type calcium channel- and/or TREK channel-associated diseases.

DETAILED DESCRIPTION OF THE EMBODIMENTS

The present inventors have studied a novel selective blocker for T-type calcium channel and/or TREK channel as an alternative to Mibefradil, and by using the technique of designing a compound on the basis of the structures of hit compounds suggested by virtual screening, they introduced (1-(substituted phenyl)-5-alkyl-1H-pyrazol-3-yl) into the structures suggested by virtual screening so as to synthesize novel derivatives, and also confirmed their efficacy, thereby completing the present invention.

To obtain various derivatives, substituted piperazine or piperidine derivative containing (R)- or (S)-1-phenoxy propan-2-ol in the molecule was designed. If (R)- or (S) epichlorohydrin commonly used as a chiral synthon is used, it is possible to control chirality. Thereafter, piperazine or piperidine containing an amide bond was introduced to obtain a desired compound.

Hereinafter, the present invention will be described in detail.

One aspect of the present invention relates to a (R)- or (S)-1-phenoxypropan-2-ol derivative having the structure of Chemical Formula I, and a racemate thereof, a pharmaceutically acceptable salt thereof, a solvate thereof and a hydrate thereof.

[Chemical Formula I]

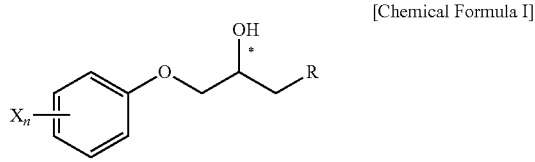

wherein * represents an (R)-form or an (S)-form,

X is selected from the group consisting of hydrogen, substituted or unsubstituted alkyl having 1 to 4 carbon atoms, and halogen, and n represents the number of X and an integer of 1 to 5, R is selected from the group consisting of compounds of the following Chemical Formulae II to VI,

[Chemical Formula II]

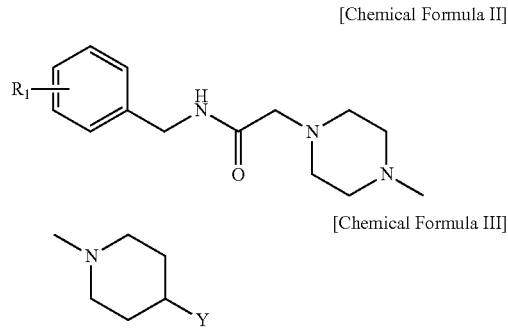

[Chemical Formula IV]

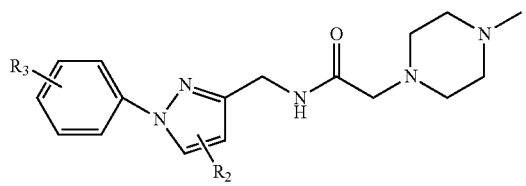

[Chemical Formula V]

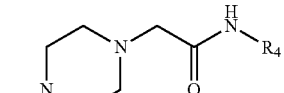

[Chemical Formula VI]

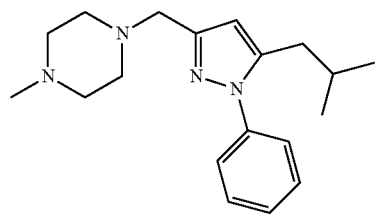

$R_1$ is a substituent binding to carbon of the phenyl group, and one or two thereof may exist, and may be each independently selected from the group consisting of hydrogen, straight or branched alkyl having 1 to 4 carbon atoms (e.g., methyl, etc.), straight or branched alkyl having 1 to 4 carbon atoms, of which one or more hydrogens are substituted with halogen (e.g., trifluoromethyl, etc.), $R_2$ may be each independently selected from the group consisting of straight or branched alkyl having 1 to 4 carbon atoms (e.g., isobutyl, isopropyl, etc.) and cycloalkyl having 3 to 8 carbon atoms (e.g., cyclopropyl, etc.), and one or two thereof may exist, $R_3$ is a substituent binding to carbon of the phenyl group, and one or two thereof may exist, and may be each independently one or more (e.g., methyl-fluoro, dichloro, etc.) selected from the group consisting of hydrogen, straight or branched alkyl having 1 to 4 carbon atoms (e.g., methyl, etc.), straight or branched alkyl having 1 to 4 carbon atoms (e.g., trifluoromethyl, etc.), of which one or more hydrogens are substituted with halogen (e.g., fluoro, etc.), and halogen (e.g., fluoro, chloro, etc.), $R_4$ may be selected from the group consisting of alkylbenzyl (wherein alkyl is straight or branched alkyl having 1 to 4 carbon atoms) (e.g., methylbenzyl, etc.), alkylbenzyl in which one or more hydrogens of the alkyl group are substituted with halogen (wherein alkyl is straight or branched alkyl having 1 to 4 carbon atoms) (e.g., trifluoromethylbenzyl, etc.), and cycloalkyl having 3 to 8 carbon atoms (e.g., cyclohexyl, etc.), Y may be selected from the group consisting of morpholine, piperidine, pyrrolidine, alkoxy phenyl (wherein alkoxy is selected from alkyl groups having 1 to 4 carbon atoms, e.g., methoxy phenyl, etc), hydroxyphenyl, hydroxyphenoxy, difluoro, and hydroxy.

The straight or branched, substituted alkyl having 1 to 4 carbon atoms of X is, for example, trifluoromethyl in which one or more of hydrogens contained in alkyl are substituted with one or more selected from the group consisting of halogen (e.g., fluoro, chloro) or the like.

In one specific embodiment of the present invention, the (R)- or (S)-1-phenoxypropan-2-ol derivative may be selected from the group consisting of the following compounds.

(R)-1-(4-((1-benzyl-1H-imidazol-2-yl)methyl)piperazin-1-yl)-3-(4-(trifluoromethyl)phenoxy)propan-2-ol,
(R)-1-(4-((1-benzyl-1H-imidazol-2-yl)methyl)piperazin-1-yl)-3-(4-fluorophenoxy)propan-2-ol,
(R)-1-(4-((1-benzyl-1H-imidazol-2-yl)methyl)piperazin-1-yl)-3-(4-fluoro)phenoxy)propan-2-ol,
(R)-N-benzyl-2-(4-(2-hydroxy-3-(p-tolyloxy)propyl)piperazin-1-yl)acetamide;
(S)-N-benzyl-2-(4-(2-hydroxy-3-(p-tolyloxy)propyl)piperazin-1-yl)acetamide;
(R)-2-(4-(2-hydroxy-3-(p-tolyloxy)propyl)piperazin-1-yl)-N-(4-methylbenzyl)acetamide;
(S)-2-(4-(2-hydroxy-3-(p-tolyloxy)propyl)piperazin-1-yl)-N-(4-methylbenzyl)acetamide;
(R)-2-(4-(2-hydroxy-3-(p-tolyloxy)propyl)piperazin-1-yl)-N-(4-(trifluoromethyl)benzyl)acetamide;
(S)-2-(4-(2-hydroxy-3-(p-tolyloxy)propyl)piperazin-1-yl)-N-(4-(trifluoromethyl)benzyl)acetamide;
(R)-N-benzyl-2-(4-(2-hydroxy-3-phenoxypropyl)piperazin-1-yl)acetamide;
(S)-N-benzyl-2-(4-(2-hydroxy-3-phenoxypropyl)piperazin-1-yl)acetamide;
(R)-2-(4-(2-hydroxy-3-phenoxypropyl)piperazin-1-yl)-N-(4-methylbenzyl)acetamide;
(S)-2-(4-(2-hydroxy-3-phenoxypropyl)piperazin-1-yl)-N-(4-methylbenzyl)acetamide;
(R)-2-(4-(2-hydroxy-3-phenoxypropyl)piperazin-1-yl)-N-(4-(trifluoromethyl)benzyl)acetamide;
(S)-2-(4-(2-hydroxy-3-phenoxypropyl)piperazin-1-yl)-N-(4-(trifluoromethyl)benzyl)acetamide;
(S)-2-(4-(2-hydroxy-3-(4-(trifluoromethyl)phenoxy)propyl)piperazin-1-yl)-N-(4-(trifluoromethyl)benzyl)acetamide;
(S)-2-(4-(2-hydroxy-3-(4-(trifluoromethyl)phenoxy)propyl)piperazin-1-yl)-N-(4-methylbenzyl)acetamide;
(S)-N-cyclohexyl-2-(4-(2-hydroxy-3-(4-(trifluoromethyl)phenoxy)propyl)piperazin-1-yl)acetamide;
(R)-N-cyclohexyl-2-(4-(2-hydroxy-3-(4-(trifluoromethyl)phenoxy)propyl)piperazin-1-yl)acetamide;
N-cyclohexyl-2-(4-(2-hydroxy-3-(4-(trifluoromethyl)phenoxy)propyl)piperazin-1-yl)acetamide;
(R)-2-(4-(2-hydroxy-3-(4-(trifluoromethyl)phenoxy)propyl)piperazin-1-yl)-N-((5-isobutyl-1-phenyl-1H-pyrazol-3-yl)methyl)acetamide;
(R)-2-(4-(2-hydroxy-3-(4-(trifluoromethyl)phenoxy)propyl)piperazin-1-yl)-N-((5-isopropyl-1-phenyl-1H-pyrazol-3-yl)methyl)acetamide;
(R)-N-((5-cyclopropyl-1-phenyl-1H-pyrazol-3-yl)methyl)-2-(4-(2-hydroxy-3-(4-(trifluoromethyl)phenoxy)propyl)piperazin-1-yl)acetamide;
(R)-2-(4-(3-(4-fluorophenoxy)-2-hydroxypropyl)piperazin-1-yl)-N-((5-isobutyl-1-phenyl-1H-pyrazol-3-yl)methyl)acetamide;
(S)-2-(4-(3-(4-fluorophenoxy)-2-hydroxypropyl)piperazin-1-yl)-N-((5-isobutyl-1-phenyl-1H-pyrazol-3-yl)methyl)acetamide;
(S)-2-(4-(2-hydroxy-3-(4-(trifluoromethyl)phenoxy)propyl)piperazin-1-yl)-N-((5-isobutyl-1-phenyl-1H-pyrazol-3-yl)methyl)acetamide;
(R)-N-((1-(5-fluoro-2-methylphenyl)-5-isobutyl-1H-pyrazol-3-yl)methyl)-2-(4-(2-hydroxy-3-(4-(trifluoromethyl)phenoxy)propyl)piperazin-1-yl)acetamide;
(R)-N-((1-(4-fluoromethyl)-5-isobutyl-1H-pyrazol-3-yl)methyl)-2-(4-(2-hydroxy-3-(4-(trifluoromethyl)phenoxy)propyl)piperazin-1-yl)acetamide;
(R)-N-((1-(3,5-dichlorophenyl)-5-isobutyl-1H-pyrazol-3-yl)methyl)-2-(4-(2-hydroxy-3-(4-(trifluoromethyl)phenoxy)propyl)piperazin-1-yl)acetamide;
(S)-N-((1-(4-fluorophenyl)-5-isobutyl-1H-pyrazol-3-yl)methyl)-2-(4-(2-hydroxy-3-(4-(trifluoromethyl)phenoxy)propyl)piperazin-1-yl)acetamide;
(S)-N-((1-(3,5-dichlorophenyl)-5-isobutyl-1H-pyrazol-3-yl)methyl)-2-(4-(2-hydroxy-3-(4-(trifluoromethyl)phenoxy)propyl)piperazin-1-yl)acetamide;
(S)-N-((1-(5-fluoro-2-methylphenyl)-5-isobutyl-1H-pyrazol-3-yl)methyl)-2-(4-(2-hydroxy-3-(4-(trifluoromethyl)phenoxy)propyl)piperazin-1-yl)acetamide;
(S)-2-(4-(2-hydroxy-3-(4-(trifluoromethyl)phenoxy)propyl)piperazin-1-yl)-N-((5-isobutyl-1-o-tolyl-1H-pyrazol-3-yl)methyl)acetamide;
(R)-N-((1-(3,5-dichlorophenyl)-5-isobutyl-1H-pyrazol-3-yl)methyl)-2-(4-(3-(4-fluorophenoxy)-2-hydroxypropyl)piperazin-1-yl)acetamide;
(R)-N-((1-(5-fluoro-2-methylphenyl)-5-isobutyl-1H-pyrazol-3-yl)methyl)-2-(4-(3-(4-fluorophenoxy)-2-hydroxypropyl)piperazin-1-yl)acetamide;
(R)-2-(4-(3-(4-fluorophenoxy)-2-hydroxypropyl)piperazin-1-yl)-N-((5-isobutyl-1-o-tolyl-1H-pyrazol-3-yl)methyl)acetamide;
(R)-2-(4-(3-(4-fluorophenoxy)-2-hydroxypropyl)piperazin-1-yl)-N-((1-(4-fluorophenyl)-5-isobutyl-1H-pyrazol-3-yl)methyl)acetamide;
(S)-2-(4-(3-(4-fluorophenoxy)-2-hydroxypropyl)piperazin-1-yl)-N-((5-isobutyl-1-o-tolyl-1H-pyrazol-3-yl)methyl)acetamide;
(S)-2-(4-(3-(4-fluorophenoxy)-2-hydroxypropyl)piperazin-1-yl)-N-((1-(4-fluorophenyl)-5-isobutyl-1H-pyrazol-3-yl)methyl)acetamide;
(S)-N-((1-(5-fluoro-2-methylphenyl)-5-isobutyl-1H-pyrazol-3-yl)methyl)-2-(4-(3-(4-fluorophenoxy)-2-hydroxypropyl)piperazin-1-yl)acetamide;
(S)-N-((1-(3,5-dichlorophenyl)-5-isobutyl-1H-pyrazol-3-yl)methyl)-2-(4-(3-(4-fluorophenoxy)-2-hydroxypropyl)piperazin-1-yl)acetamide;
(R)-1-(4-fluorophenoxy)-3-(4-morpholinopiperidin-1-yl)propan-2-ol;
(S)-1-(4-fluorophenoxy)-3-(4-morpholinopiperidin-1-yl)propan-2-ol;
(R)-1-(1,4'-bipiperidin-1'-yl)-3-(4-fluorophenoxy)propan-2-ol;
(S)-1-(1,4'-bipiperidin-1'-yl)-3-(4-fluorophenoxy)propan-2-ol;
(R)-1-(4-fluorophenoxy)-3-(4-(pyrrolidin-1-yl)piperidin-1-yl)propan-2-ol;
(S)-1-(4-fluorophenoxy)-3-(4-(pyrrolidin-1-yl)piperidin-1-yl)propan-2-ol;
(R)-1-(4-fluorophenoxy)-3-(4-(3-methoxyphenyl)piperidin-1-yl)propan-2-ol;
(S)-1-(4-fluorophenoxy)-3-(4-(3-methoxyphenyl)piperidin-1-yl)propan-2-ol;
(R)-1-(4,4-difluoropiperidin-1-yl)-3-(4-fluorophenoxy)propan-2-ol;
(R)-4-fluoro-1-(3-(4-fluorophenoxy)-2-hydroxypropyl)piperidin-4-ol;
(S)-1-(4,4-difluoropiperidin-1-yl)-3-(4-fluorophenoxy)propan-2-ol;
(S)-4-fluoro-1-(3-(4-fluorophenoxy)-2-hydroxypropyl)pyridin-4-ol;
(R)-1-(4-morpholinopiperidin-1-yl)-3-(4-(trifluoromethyl)phenoxy)propan-2-ol;
(R)-1-(1,4'-bipiperidin-1'-yl)-3-(4-(trifluoromethyl)phenoxy)propan-2-ol;
(R)-1-(4-(pyrrolidin-1-yl)piperidin-1-yl)-3-(4-(trifluoromethyl)phenoxy)propan-2-ol;

(R)-1-(4,4-difluoropiperidin-1-yl)-3-(4-(trifluoromethyl) phenoxy)propan-2-ol;
(R)-1-(2-hydroxy-3-(4-(trifluoromethyl)phenoxy)propyl)-4-phenylpiperidin-4-ol;
(S)-1-(4-morpholinopiperidin-1-yl)-3-(4-(trifluoromethyl) phenoxy)propan-2-ol;
(S)-1-(1,4'-bipiperidin-1'-yl)-3-(4-(trifluoromethyl)phenoxy)propan-2-ol;
(S)-1-(4-(pyrrolidin-1-yl)piperidin-1-yl)-3-(4-(trifluoromethyl)phenoxy)propan-2-ol;
(S)-1-(4,4-difluoropiperidin-1-yl)-3-(4-(trifluoromethyl) phenoxy)propan-2-ol; and
(S)-1-(2-hydroxy-3-(4-(trifluoromethyl)phenoxy)propyl)-4-phenylpiperidin-4-ol.

The compound of Chemical Formula I according to the present invention may be provided in the form of a racemic mixture of (R)- or (S)-form, a pharmaceutically acceptable salt thereof, a hydrate thereof, a solvate thereof, or an isomer thereof.

The 'pharmaceutically acceptable salt' may be all kinds of pharmaceutically acceptable salts derived from inorganic or organic salts or bases. For example, as the salt, an acid addition salt prepared by a pharmaceutically acceptable free acid is useful. The acid addition salts may be obtained from inorganic acids such as hydrochloric acid, nitric acid, phosphoric acid, sulfuric acid, hydrobromic acid, hydroiodic acid, nitrous acid and phosphorous acid; and non-toxic organic acids such as aliphatic mono- and di-carboxylate, phenyl-substituted alkanoate, hydroxy alkanoate and alkandioate, aromatic acids, aliphatic and aromatic sulfonic acids. The pharmaceutically available salt may includes sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propionate, oxalate, malonate, succinate, suberate, sebacate, fumarate, maleate, butyne-1,4-dioate, hexane-1,6-dioate, benzoate, chlorobenzoate, methyl benzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, maleate, tartrate, methane sulfonate, propanesulfonate, naphthalene-1-sulfonate, naphthalene-2-sulfonate and mandelate.

The term 'solvate', as used herein, refers to a molecular complex of the compound of Chemical Formula I and a pharmaceutically acceptable solvent, for example, a lower alcohol having 1 to 4 carbon atoms, and the term 'hydrate' refers to a molecular complex of the compound of Chemical Formula I and water.

Further, the scope of the compound of the present invention can be extended to the form which is introduced with a protecting group or a deprotecting group generally known. If an optical isomer is present in the compound, enantiomers, diastereomers, or racemic mixture thereof are also included.

As confirmed in Experimental Examples 1 and 2, the compound of Chemical Formula I of the present invention shows excellent T-type calcium channel and TREK-1 channel-blocking and/or inhibiting activity, which is equivalent to or higher than that of the control drug.

Therefore, the compound of Chemical Formula I of the present invention can be effectively used as a blocker of T-type calcium channel and/or TREK-1 channel.

Accordingly, another aspect of the present invention provides use of the blocker including the compound of Chemical Formula I of the present invention, and/or a pharmaceutically acceptable salt thereof, a hydrate thereof, a solvate thereof, and/or an isomer thereof as an active ingredient for blocking and/or inhibiting T-type calcium channel and/or TREK-1 channel.

In detail, the composition including the compound of Chemical Formula I, and/or the pharmaceutically acceptable salt thereof, the hydrate thereof, the solvate thereof, and/or the isomer thereof as an active ingredient is provided as a composition for blocking and/or inhibiting T-type calcium channel and/or TREK-1 channel. Still another aspect provides a method for blocking and/or inhibiting T-type calcium channel and/or TREK-1 channel, including the steps of preparing a biological sample separated from the living body; and applying the compound of Chemical Formula I, and/or the pharmaceutically acceptable salt thereof, the hydrate thereof, the solvate thereof, and/or the isomer thereof to the biological sample. The biological sample means a sample separated from the living body, such as cells, tissues, blood, saliva, other body fluid derived from a mammal, preferably a human.

Further, overexpression and/or overactivation of T-type calcium channel and/or TREK-1 channel cause(s) many different diseases, and still another aspect of the present invention provides a pharmaceutical composition including the compound of Chemical Formula I, and/or the pharmaceutically acceptable salt thereof, the hydrate thereof, the solvate thereof, and/or the isomer thereof as an active ingredient for the prevention and/or treatment of T-type calcium channel and/or TREK-1 channel-associated diseases.

Still another aspect of the present invention provides a food composition including the compound of Chemical Formula I, and/or the pharmaceutically acceptable salt thereof, the hydrate thereof, the solvate thereof, and/or the isomer thereof as an active ingredient for the prevention and/or improvement of T-type calcium channel and/or TREK-1 channel-associated diseases.

As described above, it has been reported that the T-type calcium channel is involved in bursting firing of nerve cells (Huguenard, J. R. et al., Annu. Rev. Physiol. 1996, 58, 329-348), pacemaker activity of the heart (Zhou, Z. et al., J. Mol. Cell. Cardiol. 1994, 26, 1211-1219), secretion of the hormone aldosterone (Rossier, M. F. et al., Endocrinology 1996, 137, 4817-4826), and fertilization (Arnoult, C. et al., Proc. Natl. Acad. Sci. 1996, 93, 13004-13009). It is known that overexpression of the T-type calcium channel may cause diseases such as epilepsy (Tsakiridou, E. et al., J. Neurosci. 1995, 15, 3110-3117), high blood pressure (Self, D. A. et al., J. Vacs. Res. 1994, 31, 359-366), ventricular hypertrophy (Nuss, H. B. et al., Circ. Res. 1995, 73, 777-7825), pain (Shin, H. S. et al., Science 2003, 302, 117-119), and angina pectoris (Van der Vring, J. A. et al., Am. J. Ther. 1999, 6, 229-233). In particular, it has been also reported that the T-type calcium channel is involved in pain relief (Ikeda, H. et al., Science 2003, 299, 1237-1240). The inhibitors against these channels are already commercially available as various anodynes (Schaible, Prog. Brain Res., 2000, 129:173-190).

It has been also reported that overexpression and/or overactivation of TREK-1 (KCNK2, potassium channel, subfamily K, member 2) channel cause(s) hypoxia (Kemp P J, Peers C, Lewis A, Miller P, J Cell Mol Med. 2004 January-March; 8(1): 38-44, 'Regulation of recombinant human brain tandem P domain K$^+$ channels by hypoxia: a role for O2 in the control of neuronal excitability'), brain ischemia (Xu X, Pan Y, Wang X, Brain Res Mol Brain Res. 2004 Jan. 5; 120(2): 205-9, 'Alterations in the expression of lipid and mechano-gated two-pore domain potassium channel genes in rat brain following chronic cerebral ischemia'), alkalosis (Miller P, Peers C, Kemp P J, Am J Physiol Cell Physiol. 2004 February; 286(2): C272-82, Epub 2003 Oct. 1, 'Polymodal regulation of hTREK1 by pH, arachidonic acid, and hypoxia: physiological impact in acidosis and alkalosis'), depression (Heurteaux C, Lucas G, Guy N, El Yacoubi M, Thummler S, Peng X D, Noble F, Blondeau N, Widmann C, Borsotto M, Gobbi G, Vaugeois J M, Debonnel G, Lazdunski M, Nat Neurosci. 2006 September; 9(9): 1134-41. Epub 2006 Aug. 13, 'Deletion of the background potassium channel TREK-1 results in a depression-resistant phenotype'; Gordon J A, Hen R, Nat Neurosci. 2006 September; 9(9):1081-3), 'TREKing toward new antidepressants', Liou Y J, Chen T J, Tsai S J, Yu Y W, Cheng C Y, Hong C J, Pharmacogenet Genomics. 2009 October; 19(10):735-41, 'Support for the involvement of the KCNK2 gene in major depressive disorder and response to antidepressant treatment'), prostate cancer (Voloshyna I, Besana A, Castillo M, Matos T, Weinstein I B, Mansukhani M, Robinson R B, Cordon-Cardo C, Feinmark S J, Cancer Res. 2008 Feb. 15; 68(4):1197-203, 'TREK-1 is a novel molecular target in prostate cancer'), high blood pressure (Pokojski S, Busch C, Grgic I, Kacik M, Salman W, Preisig-Muller R, Heyken W T, Daut J, Hoyer J, Kohler R, Cardiovasc Res. 2008 Jul. 1; 79(1):80-8. Epub 2008 Mar. 13, 'TWIK-related two-pore domain potassium channel TREK-1 in carotid endothelium of normotensive and hypertensive mice') or the like.

Therefore, the T-type calcium channel and/or TREK-1 channel-associated diseases which can be prevented and/or improved and/or treated by the compound of Chemical Formula I of the present invention, and/or the pharmaceutically acceptable salt thereof, the hydrate thereof, the solvate thereof, and/or the isomer thereof may be Parkinson's disease, Alzheimer's disease, schizophrenia, dyssomnia, epilepsy, pain, high blood pressure, arrhythmia, angina pectoris, heart failure, myocardial infarction, cancer, hypoxia, brain ischemia, alkalosis, prostate cancer, depression or the like.

The content of the compound of Chemical Formula I, the pharmaceutically acceptable salt thereof, the hydrate thereof, the solvate thereof, and/or the isomer thereof which is an active ingredient in the pharmaceutical composition of the present invention can be properly controlled depending on severity and symptoms of the disease, and conditions of a patient to be applied. For example, the content may be 0.001 to 99.9% by weight, for example, 0.01 to 90% by weight, 0.1 to 70% by weight, and preferably 1 to 50% by weight, based on the total weight of the composition, but is not limited thereto.

The pharmaceutical composition may further include a proper carrier, excipient, and diluent which are typically used in the preparation of the pharmaceutical composition. The pharmaceutical composition may be formulated as an oral dosage form such as a powder, a granule, a tablet, a capsule, a suspension, an emulsion, a syrup, an aerosol or the like, an external preparation, a suppository or a sterile injection solution, or the like.

The pharmaceutical composition may be formulated using commonly used diluents or excipients such as a filler, a bulking agent, a binder, a wetting agent, a disintegrating agent, surfactant or the like. A solid preparation for oral administration may include a tablet, a pill, a powder, a granule, a capsule or the like, and the solid preparation may include at least one excipient and/or lubricant or the like. A liquid preparation for oral administration may include a suspension, a liquid for internal use, an emulsion, a syrup or the like, and it may include various excipients, for example, a wetting agent, a sweetener, a flavoring agent, a preservative or the like, in addition to commonly used simple diluent such as water, liquid paraffin. A preparation for parenteral administration may include an injectable formulation, a sterilized aqueous solution, a non-aqueous solvent, a suspension, an emulsion, a freeze-dried preparation, a suppository or the like.

Preferred dosage of the composition may be determined according to the degree of disease, symptoms, a patient's body weight, the type of drug, administration route and period or the like. For more preferable effects, the composition of the present invention may be administered at a daily dosage of 0.1 mg/kg to 1000 mg/kg, preferably 1 to 500 mg/kg, based on the weight of the active ingredient, but is not limited thereto. It may be administered once a day or it may be dividedly administered several times a day. The composition of the present invention may be administered to animals, preferably mammals including human, or birds by various routes. For example, it may be administered by oral, intravenous, intramuscular or subcutaneous injection or the like, and all the other possible administration routes may be applied. The pharmaceutical dosage form of the composition of the present invention may be a pharmaceutically acceptable salt of the active ingredient, and it may be administered alone or in combination with other pharmaceutically active compounds as well as in conjunction therewith.

The phenoxypropanol derivative having the structure of Chemical Formula I according to the present invention effectively inhibits T-type calcium channel or TREK-1 channel, and thus it is very useful for the treatment of various diseases caused by activation thereof.

EXAMPLE

The invention will be described in more detail by examples. The following examples are intended to merely illustrate the present invention, and the scope of the invention is not limited by them in any ways.

Example 1

The phenoxypropanol derivative were prepared by the process indicated in reaction scheme 1.

[Reaction Scheme 1]

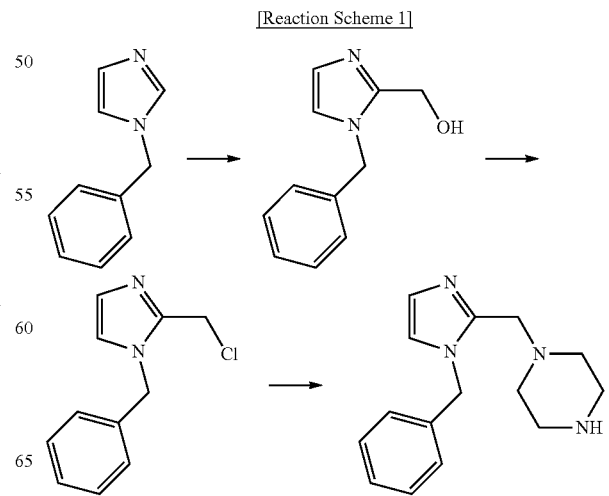

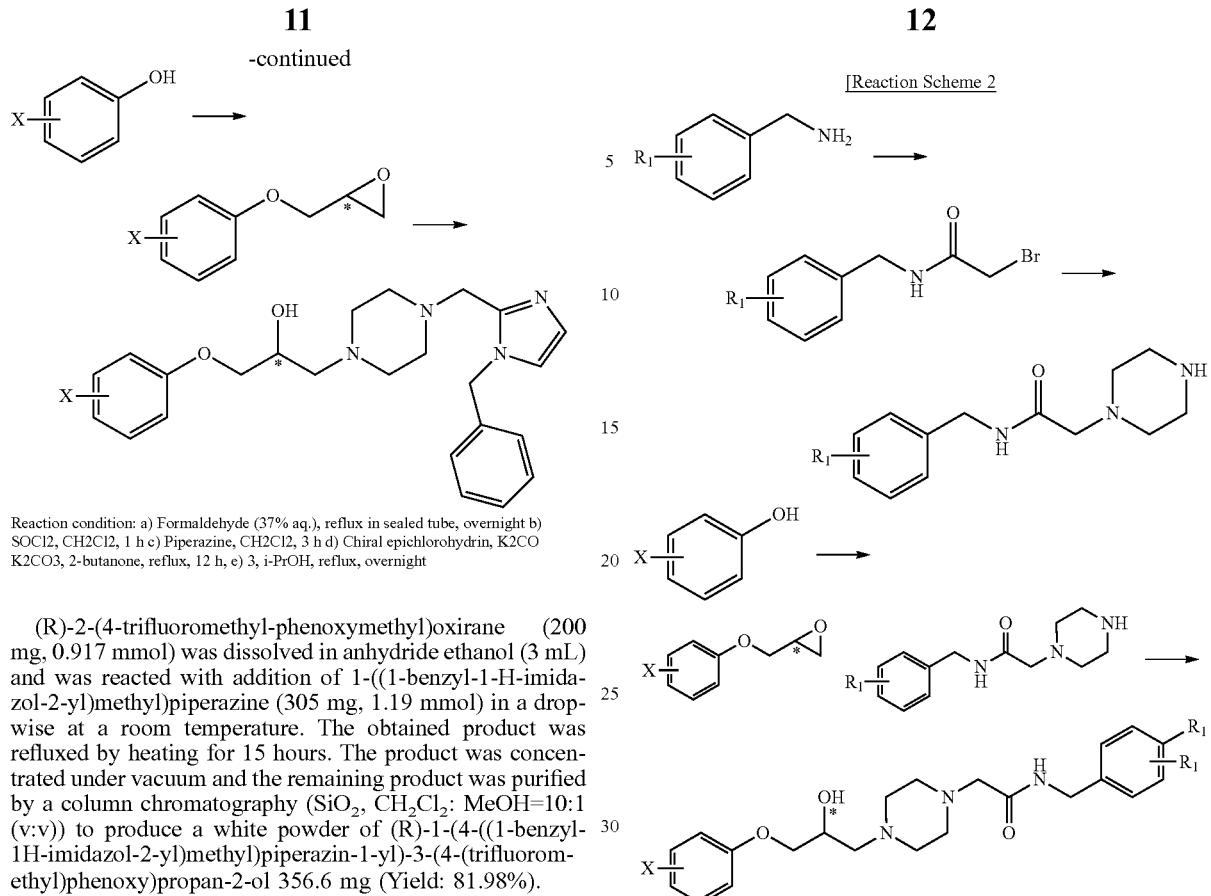

Reaction condition: a) Formaldehyde (37% aq.), reflux in sealed tube, overnight b) SOCl2, CH2Cl2, 1 h c) Piperazine, CH2Cl2, 3 h d) Chiral epichlorohydrin, K2CO K2CO3, 2-butanone, reflux, 12 h, e) 3, i-PrOH, reflux, overnight (R)-2-(4-trifluoromethyl-phenoxymethyl)oxirane (200 mg, 0.917 mmol) was dissolved in anhydride ethanol (3 mL) and was reacted with addition of 1-((1-benzyl-1-H-imidazol-2-yl)methyl)piperazine (305 mg, 1.19 mmol) in a dropwise at a room temperature. The obtained product was refluxed by heating for 15 hours. The product was concentrated under vacuum and the remaining product was purified by a column chromatography (SiO$_2$, CH$_2$Cl$_2$: MeOH=10:1 (v:v)) to produce a white powder of (R)-1-(4-((1-benzyl-1H-imidazol-2-yl)methyl)piperazin-1-yl)-3-(4-(trifluoromethyl)phenoxy)propan-2-ol 356.6 mg (Yield: 81.98%).

KKRE10153: (R)-1-(4-((1-benzyl-1H-imidazol-2-yl)methyl)piperazin-1-yl)-3-(4-(trifluoromethyl)phenoxy)propan-2-ol (X=trifluoromethyl)

Yield: 81.98%, $^1$H-NMR (400 MHz, CDCl$_3$) δ=2.52-2.64 (m, 8H, 4CH$_2$), 2.68 (br s, 2H, CH$_2$), 3.57 (s, 2H, CH$_2$), 4.03 (d, 2H, J=9.96 Hz, CH$_2$), 4.11-4.16 (m, 1H, CH), 5.27 (s, 2H, CH$_2$), 6.90 (s, 1H, CH (imidazole)), 6.97 (s, 1H, CH(imidazole), 6.99-7.55 (m, 9H, Ph)

In accordance with the same method as described above, methyl-phenoxymethyl)oxirane as X substituent was used for producing the following compounds:

KKRE10154: (R)-1-(4-((1-benzyl-1H-imidazol-2-yl)methyl)piperazin-1-yl)-3-(4-fluorophenoxy)propan-2-ol (X=fluoro)

Yield: 84.89%, $^1$H-NMR (400 MHz, CDCl$_3$) δ=2.50-2.62 (m, 8H, 4CH$_2$), 2.66 (br s, 2H, CH$_2$), 3.56 (s, 2H, CH$_2$), 3.93 (dd, 2H, J$_1$=1.8 Hz, J$_1$=4.9 Hz, CH$_2$), 4.07-4.11 (m, 1H, CH), 5.26 (s, 2H, CH$_2$), 6.83-6.85 (m, 2H, 2CH (imidazole)), 6.90-7.36 (m, 9H, Ph)

KKRE10155
(R)-1-(4-((1-benzyl-1H-imidazol-2-yl)methyl)piperazin-1-yl)-3-(4-fluorophenoxy)propan-2-ol Yield: 85.38%, $^1$H-NMR (400 MHz, CDCl$_3$) δ=2.50-2.62 (m, 8H, 4CH$_2$), 2.66 (br s, 2H, CH$_2$), 3.56 (s, 2H, CH$_2$), 3.93 (dd, 2H, J$_1$=1.8 Hz, J$_1$=4.9 Hz, CH$_2$), 4.07-4.11 (m, 1H, CH), 5.26 (s, 2H, CH$_2$), 6.83-6.85 (m, 2H, 2CH (imidazole)), 6.90-7.36 (m, 9H, Ph)

Example 2

The phenoxypropanol derivative were prepared by the process indicated in reaction scheme 2

2-(p-tolylmethyl)oxirane (70.4 mg, 0.4286 mmol) and N-benzyl-2-(piperazin-1-yl)acetamide (100 mg, 0.429 mmol) were dissolved in methanol 3 mL, and centrifuged at 800 rpm at a temperature of 60° C. for 15 hours. The obtain product was concentrated under vacuum and the remaining product was purified by a column chromatography (SiO$_2$, eluent Ethylacetate only) to produce a solid form of (R)-N-benzyl-2-(4-(2-hydroxy-3-(p-tolyloxy)propyl)piperazin-1-yl)acetamide 104.5 mg (Yield: 61.34%).

KKRE10196:
R)-N-benzyl-2-(4-(2-hydroxy-3-(p-tolyloxy)propyl)piperazin-1-yl)acetamide (R$_1$=H, X=methyl)

Yield: 61.34%, $^1$H NMR (400 MHz, CDCl$_3$) δ=2.28 (s, 3H, Me), 2.50 (m, 2H, CH$_2$), 2.53 (m, 2H, CH$_2$), 2.56-2.59 (m, 4H, CH$_2$), 2.66 (brs, 2H, CH$_2$), 3.09 (s, 2H, PhCH$_2$NH), 3.95 (d, 2H, J=4.92 Hz, CH$_2$), 4.04-4.08 (m, 1H, CH), 4.49 (d, 2H, J=6.02 Hz, CH$_2$), 6.80-7.37 (m, 9H, 2Ph), 7.44 (brs, 1H, NH)

In accordance with the same method as described above, 2-(4-substituted oxymethyl)oxirane and N-(4-substituted benzyl)-2-(piperazin-1-yl)acetamide as R1 and X substituent were used for producing the following compounds:

KKRE10197
S)-N-benzyl-2-(4-(2-hydroxy-3-(p-tolyloxy)propyl)piperazin-1-yl)acetamide (R$_1$=H, X=methyl)

Yield: 65.09%, $^1$H NMR (400 MHz, CDCl$_3$) δ=2.28 (s, 3H, Me), 2.50 (m, 2H, CH$_2$), 2.53 (m, 2H, CH$_2$), 2.56-2.59 (m, 4H, CH$_2$), 2.66 (brs, 2H, CH$_2$), 3.09 (s, 2H, PhCH$_2$NH), 3.95 (d, 2H, J=4.90 Hz, CH$_2$), 4.04-4.08 (m, 1H, CH), 4.49 (d, 2H, J=6.01 Hz, CH$_2$), 6.80-7.37 (m, 9H, 2Ph), 7.43 (brs, 1H, NH)

KKRE10198

(R)-2-(4-(2-hydroxy-3-(p-tolyloxy)propyl)piperazin-1-yl)-N-(4-methylbenzyl)acetamide (R₁=methyl, X=methyl)

Yield: 53.91%,

¹H NMR (400 MHz, CDCl₃) δ=2.28 (s, 6H, 2Me), 2.50 (m, 2H, CH₂), 2.53 (m, 2H, CH₂), 2.56-2.59 (m, 4H, CH₂), 2.66 (brs, 2H, CH₂), 3.09 (s, 2H, PhCH₂NH), 3.95 (d, 2H, J=4.90 Hz, CH₂), 4.04-4.08 (m, 1H, CH), 4.49 (d, 2H, J=6.01 Hz, CH₂), 6.80-7.37 (m, 9H, 2Ph), 7.43 (brs, 1H, NH)

KKRE10199

(S)-2-(4-(2-hydroxy-3-(p-tolyloxy)propyl)piperazin-1-yl)-N-(4-methylbenzyl)acetamide (R₁=methyl, X=methyl)

Yield: 85.04%,

¹H NMR (400 MHz, CDCl₃) δ=2.28 (s, 6H, 2Me), 2.50 (m, 2H, CH₂), 2.53 (m, 2H, CH₂), 2.56-2.59 (m, 4H, CH₂), 2.66 (brs, 2H, CH₂), 3.09 (s, 2H, PhCH₂NH), 3.95 (d, 2H, J=4.90 Hz, CH₂), 4.04-4.08 (m, 1H, CH), 4.49 (d, 2H, J=6.01 Hz, CH₂), 6.80-7.37 (m, 9H, 2Ph), 7.43 (brs, 1H, NH)

KKRE10200

(R)-2-(4-(2-hydroxy-3-(p-tolyloxy)propyl)piperazin-1-yl)-N-(4-(trifluoromethyl)benzyl)acetamide (R₁=trifluoromethyl, X=methyl)

Yield: 55.81%,

¹H NMR (400 MHz, CDCl₃) δ=2.87 (s, 3H, Me), 2.50 (m, 2H, CH₂), 2.54 (m, 2H, CH₂), 2.58-2.61 (m, 4H, CH₂), 2.67 (brs, 2H, CH₂), 3.10 (s, 2H, PhCH₂NH), 3.95 (d, 2H, J=4.94 Hz, CH₂), 4.04-4.09 (m, 1H, CH), 4.54 (d, 2H, J=6.23 Hz, CH₂), 6.80-7.61 (m, 8H, 2Ph), 7.54 (brs, 1H, NH)

KKRE10201

(S)-2-(4-(2-hydroxy-3-(p-tolyloxy)propyl)piperazin-1-yl)-N-(4-(trifluoromethyl)benzyl)acetamide (R₁=trifluoromethyl, X=methyl)

Yield: 63.93%,

¹H NMR (400 MHz, CDCl₃) δ=2.87 (s, 3H, Me), 2.50 (m, 2H, CH₂), 2.54 (m, 2H, CH₂), 2.58-2.61 (m, 4H, CH₂), 2.67 (brs, 2H, CH₂), 3.10 (s, 2H, PhCH₂NH), 3.95 (d, 2H, J=4.96 Hz, CH₂), 4.04-4.09 (m, 1H, CH), 4.54 (d, 2H, J=6.20 Hz, CH₂), 6.80-7.61(m, 8H, 2Ph), 7.54 (brs, 1H, NH)

KKRE10202

(R)-N-benzyl-2-(4-(2-hydroxy-3-phenoxypropyl)piperazin-1-yl)acetamide (R₁=H, X=H)

Yield: 43.04%,

¹H NMR (400 MHz, CDCl₃) δ=2.51 (m, 2H, CH₂), 2.54 (m, 2H, CH₂), 2.57-2.60 (m, 4H, CH₂), 2.66 (brs, 2H, CH₂), 3.09 (s, 2H, PhCH₂NH), 3.98 (d, 2H, J=4.92 Hz, CH₂), 4.05-4.15 (m, 1H, CH), 4.50 (d, 2H, J=6.02 Hz, CH₂), 6.91-7.43 (m, 10H, 2Ph), 7.43 (brs, 1H, NH)

KKRE10203

(S)-N-benzyl-2-(4-(2-hydroxy-3-phenoxypropyl)piperazin-1-yl)acetamide (R₁=H, X=H)

Yield: 55.34%,

¹H NMR (400 MHz, CDCl₃) δ=2.51 (m, 2H, CH₂), 2.54 (m, 2H, CH₂), 2.57-2.60 (m, 4H, CH₂), 2.67 (brs, 2H, CH₂), 3.09 (s, 2H, PhCH₂NH), 3.98 (d, 2H, J=4.9 Hz, CH₂), 4.05-4.13 (m, 1H, CH), 4.50 (d, 2H, J=6.0 Hz, CH₂), 6.91-7.42 (m, 10H, 2Ph), 7.43 (brs, 1H, NH)

KKRE10204

(R)-2-(4-(2-hydroxy-3-phenoxypropyl)piperazin-1-yl)-N-(4-methylbenzyl)acetamide (R₁=methyl, X=H)

Yield: 82.01%,

¹H NMR (400 MHz, CDCl₃) δ=2.51 (m, 2H, CH₂), 2.54 (m, 2H, CH₂), 2.57-2.60 (m, 4H, CH₂), 2.66 (brs, 2H, CH₂), 3.09 (s, 2H, PhCH₂NH), 3.98 (d, 2H, J=4.92 Hz, CH₂), 4.05-4.15 (m, 1H, CH), 4.50 (d, 2H, J=6.02 Hz, CH₂), 6.91-7.43 (m, 8H, 2Ph), 7.43 (brs, 1H, NH)

KKRE10205

(S)-2-(4-(2-hydroxy-3-phenoxypropyl)piperazin-1-yl)-N-(4-methylbenzyl)acetamide (R₁=methyl, X=H)

Yield: 26.61%,

¹H NMR (400 MHz, CDCl₃) δ=2.51 (m, 2H, CH₂), 2.54 (m, 2H, CH₂), 2.57-2.60 (m, 4H, CH₂), 2.66 (brs, 2H, CH₂), 3.09 (s, 2H, PhCH₂NH), 3.98 (d, 2H, J=4.92 Hz, CH₂), 4.05-4.15 (m, 1H, CH), 4.50 (d, 2H, J=6.02 Hz, CH₂), 6.91-7.43 (m, 8H, 2Ph), 7.43 (brs, 1H, NH)

KKRE10206

(R)-2-(4-(2-hydroxy-3-phenoxypropyl)piperazin-1-yl)-N-(4-(trifluoromethyl)benzyl)acetamide (R₁=trifluoromethyl, X=H)

Yield: 55.14%,

¹H NMR (400 MHz, CDCl₃) δ=2.51 (m, 2H, CH₂), 2.54 (m, 2H, CH₂), 2.57-2.60 (m, 4H, CH₂), 2.66 (brs, 2H, CH₂), 3.09 (s, 2H, PhCH₂NH), 3.98 (d, 2H, J=4.92 Hz, CH₂), 4.05-4.15 (m, 1H, CH), 4.50 (d, 2H, J=6.02 Hz, CH₂), 6.80-7.08 (m, 4H, Ph), 7.43 (brs, 1H, NH)

KKRE10207

(S)-2-(4-(2-hydroxy-3-phenoxypropyl)piperazin-1-yl)-N-(4-(trifluoromethyl)benzyl)acetamide (R₁=trifluoromethyl, X=H)

Yield: 58.13%,

¹H NMR (400 MHz, CDCl₃) δ=2.51 (m, 2H, CH₂), 2.54 (m, 2H, CH₂), 2.57-2.60 (m, 4H, CH₂), 2.66 (brs, 2H, CH₂), 3.09 (s, 2H, PhCH₂NH), 3.98 (d, 2H, J=4.92 Hz, CH₂), 4.05-4.15 (m, 1H, CH), 4.50 (d, 2H, J =6.02 Hz, CH₂), 6.80-7.08 (m, 4H, Ph), 7.43 (brs, 1H, NH)

Example 3

The phenoxypropanol derivative were prepared by the process indicated in reaction scheme 3.

[Reaction Scheme 3]

Scheme 1.

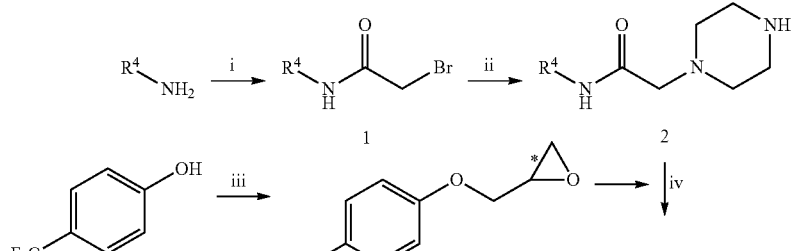

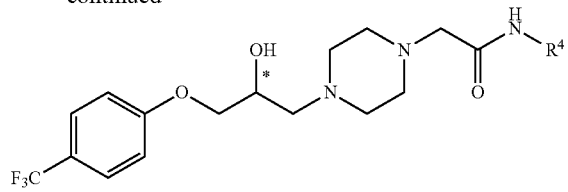

4

Reagents and conditions: i) Bromoacetylbromide, CH$_2$Cl$_2$, rt, ii) Piperazine (5 eq), CH$_2$Cl$_2$, rt, iii) Epichlorohydrin (R, S, racemic), K$_2$CO$_3$, 2-butanone, reflux, iv) MeOH, rt Compound 3 (150 mg, 0.73 mmol, (S) type) was dissolved in anhydride methanol 3 mL and was added slowly by Compound 2 (221 mg, 0.73 mmol, R4: 4-Trifluoromethylbenzyl). The reaction mixture was agitated at 700 rpm at a room temperature for 12 hours and the solvent was removed by vacuum evaporation method, and purified by a column chromatography (EtOAc:n-Hex=2:3 (v:v)) to produce a while powder of Compound 4((S)-2-(4-(2-hydroxy-3-(4-(trifluoromethyl)phenoxy)propyl)piperazin-1-yl)-N-(4-(trifluoromethyl)benzyl)acetamide, (Yield: 41%).

KKRE10173

(S)-2-(4-(2-hydroxy-3-(4-(trifluoromethyl)phenoxy)propyl)piperazin-1-yl)-N-(4-(trifluoromethyl)benzyl)acetamide (R4=4-Trifluoromethylbenzyl)

Yield: 41%, $^1$H-NMR (400 MHz, CDCl$_3$) δ=2.50-2.69 (m, 10H), 3.09 (s, 2H), 3.99-4.03 (m, 2H), 4.07-4.11 (m, 1H), 4.53 (d, 2H, J=6.16 Hz), 6.96 (d, 2H, J=8.64 Hz), 7.37 (d, 2H, J=8.00 Hz), 7.52 (d, 2H, J=8.76 Hz), 7.58 (d, 2H, J=8.12 Hz)

In accordance with the same method as described above, Compound 2 as R4 substituent were used for producing the following compounds:

KKRE10174

(S)-2-(4-(2-hydroxy-3-(4-(trifluoromethyl)phenoxy)propyl)piperazin-1-yl)-N-(4-methylbenzyl)acetamide (R4=4-Methylbenzyl)

Yield: 54%, $^1$H-NMR (400 MHz, CDCl$_3$) δ=2.34 (s, 3H), 2.50-2.77 (m, 10H), 3.09 (s, 2H), 3.99-4.05 (m, 2H), 4.15-4.18 (m, 1H), 4.44 (d, 2H, J=5.92 Hz), 6.96 (d, 2H, J=8.60 Hz), 7.13-7.18 (m, 4H), 7.30 (bs, 1H), 7.54 (d, 2H, J=8.64 Hz)

KKRE10175

(S)-N-cyclohexyl-2-(4-(2-hydroxy-3-(4-(trifluoromethyl)phenoxy)propyl)piperazin-1-yl)acetamide (R4=Cyclohexyl)

Yield: 36%, $^1$H-NMR (400 MHz, CDCl$_3$) δ=1.16-1.21 (m, 2H), 1.38-1.41 (m, 2H), 1.67-1.71 (m, 4H), 1.87-1.90 (m, 2H), 2.66-2.83 (m, 10H), 3.03 (s, 2H), 3.79-3.83 (m, 1H), 4.02-4.05 (m, 2H), 4.18-4.21 (m, 1H), 6.98 (d, 2H, J=8.68 Hz), 7.55 (d, 2H, J=8.76 Hz)

KKRE10176

(R)-N-cyclohexyl-2-(4-(2-hydroxy-3-(4-(trifluoromethyl)phenoxy)propyl)piperazin-1-yl)acetamide (R4=Cyclohexyl)

Yield: 57%, $^1$H-NMR (400 MHz, CDCl$_3$) δ=1.16-1.21 (m, 2H), 1.37-1.41 (m, 2H), 1.66-1.71 (m, 4H), 1.86-1.90 (m, 2H), 2.57-2.76 (m, 10H), 3.00 (s, 2H), 3.76-3.83 (m, 1H), 4.03 (d, 2H, J=4.84 Hz), 4.11-4.15 (m, 1H), 6.98 (d, 2H, J=8.64 Hz), 7.54 (d, 2H, J=8.76 Hz)

KKRE10177

N-cyclohexyl-2-(4-(2-hydroxy-3-(4-(trifluoromethyl)phenoxy)propyl)piperazin-1-yl)acetamide (R4=Cyclohexyl)

Yield: 66%, $^1$H-NMR (400 MHz, CDCl$_3$) δ=1.16-1.21 (m, 2H), 1.37-1.41 (m, 2H), 1.67-1.71 (m, 4H), 1.86-1.90 (m, 2H), 2.56-2.76 (m, 10H), 3.00 (s, 2H), 3.76-3.82 (m +, 1H), 4.03 (d, 2H, J=4.84 Hz), 4.11-4.15 (m, 1H), 6.98 (d, 2H, J=8.64 Hz), 7.54 (d, 2H, J=8.76 Hz)

Example 4

The phenoxypropanol derivative were prepared by the process indicated in reaction scheme 4.

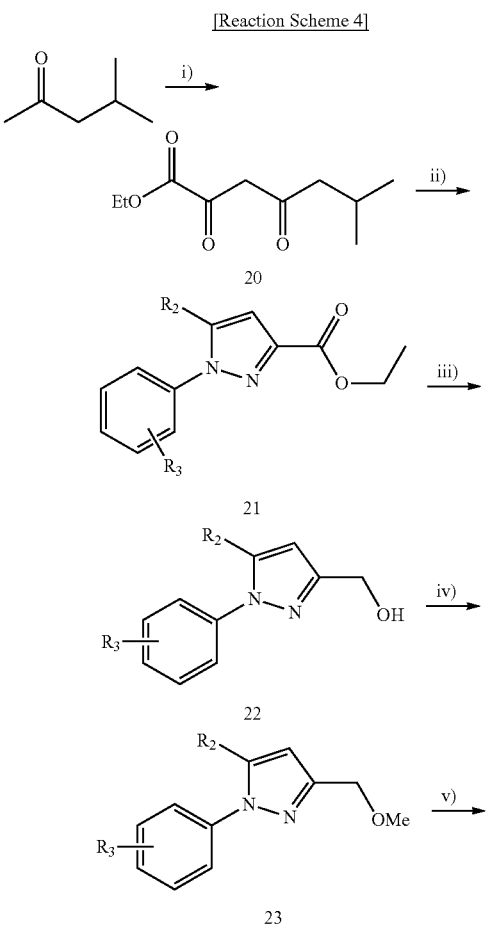

[Reaction Scheme 4]

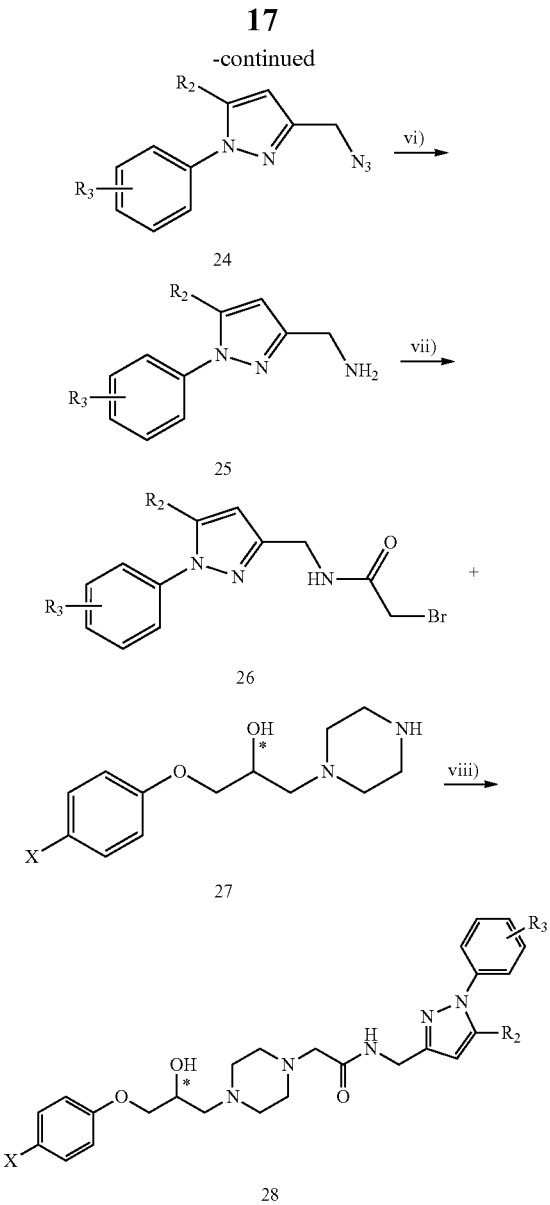

Reagents and Conditions: i) Diethyl oxalate, NaOEt, EtOH, 0° C. to rt; ii) Phenylhydrazine derivatives, EtOH, 0° C. to rt; iii) LiAlH₄, THF, 0° C. to rt; iv) MsCl, Et₃N, CH₂Cl₂, 0° C. to rt; v) Sodium azide, DMF, 50° C.; vi) H₂, Pd/C, MeOH, rt; vii) Bromoacetyl bromide Et₃N, CH₂Cl₂; viii) K₂CO₃, CH₃CN, reflux Compound 27 (300 mg, 0.97 mmol, X=trifluoromethyl) was dissolved ahhydride CH₃CN 5 mL and was added by potassium carbonate (225 mg, 1.62 mmol) and Compound 26 (300 mg, 0.81 mmol, R2=isobutyl, R3=H). The reaction mixture was refluxed by heating for 4 hours and then the sediment product was filtrated and evaporated under vacuum, and extracted by using methylene chloride and water. The product was dried by using sodium sulfate anhydride and purified by Column chromatography (MC: MeOH=20:1 (v/v)) to produce a white solid of Compound 28 ((R)-2-(4-(2-Hydroxy-3-(4-(trifluoromethyl)phenoxy) propyl)piperazin-1-yl)-N-((5-isobutyl-1-phenyl-1H-pyrazol-3-yl)methyl)acetamide) (Yield: 90%, white solid).

KKRE10210

(R)-2-(4-(2-Hydroxy-3-(4-(trifluoromethyl)phenoxy)propyl)piperazin-1-yl)-N-((5-isobutyl-1-phenyl-1H-pyrazol-3-yl)methyl)acetamide (X=trifluoromethyl, R2=isobutyl, R3=H)

Yield: 90%, $^1$H-NMR (400 MHz, CDCl₃) δ=0.85-0.87 (6H, d, J=6.61 Hz, 2CH₃), 1.78-1.88 (1H, m, CH), 2.50-2.52 (2H, d, J=7.18 Hz, CH₂), 2.56-2.84 (10H, m, 5CH₂), 3.70 (2H, s, CH₂), 4.01-4.02 (2H, d, J=4.87 Hz, CH₂), 4.12-4.17 (1H, m, CH), 6.24 (1H, s, Ar), 6.97-6.99 (2H, d, J=8.66 Hz, 2Ph), 7.37-7.40 (3H, m, 3Ph), 7.44-7.48 (2H, m, 2Ph), 7.53-7.55 (2H, d, J=8.70 Hz, 2Ph)

In accordance with the same method as described above, Compound 26 and Compound 27 as R3 and X substituents were used for producing the following compounds:

KKRE10211

(R)-2-(4-(2-hydroxy-3-(4-(trifluoromethyl)phenoxy)propyl)piperazin-1-yl)-N-((5-isopropyl-1-phenyl-1H-pyrazol-3-yl)methyl)acetamide (X=trifluoromethyl, R2=isopropyl, R3=H)

Yield: 86%, $^1$H-NMR (400MHz, CDCl₃) δ=1.17 (d, 6H, J=6.84 Hz), 2.46-2.66 (m, 10H), 3.02 (m, 1H), 3.08 (s, 2H), 4.01-4.11 (m, 3H), 4.51 (d, 2H, J=5.68 Hz), 6.15 (s, 1H), 6.98 (d, 2H, J=8.68 Hz), 7.39-7.42 (m, 3H), 7.45-7.49 (m, 2H), 7.54 (d, 2H, J=8.72 Hz), 7.67 (bs, 1 H)

KKRE10212

(R)-N-((5-cyclopropyl-1-phenyl-1H-pyrazol-3-yl)methyl)-2-(4-(2-hydroxy-3-(4-(trifluoromethyl)phenoxy)propyl)piperazin-1-yl)acetamide (X=trifluoromethyl, R2=cyclopropyl, R3=H)

Yield: 83%, $^1$H-NMR (400MHz, CDCl₃) δ=0.74-0.78 (m, 2H), 0.97-1.00 (m, 2H), 1.79 (m, 1H), 2.69-3.04 (m, 10H), 3.13 (s, 2H), 3.97-4.09 (m, 2H), 4.32 (bs, 1H), 4.48 (d, 2H, J=5.60 Hz), 5.89 (s, 1H), 6.97 (d, 2H, J=8.64 Hz), 7.35 (t, 1H, J=7.42 Hz), 7.48 (t, 2H, J=7.84 Hz), 7.55-7.60 (m, 1H)

KKRE10213

(R)-2-(4-(3-(4-Fluorophenoxy)-2-hydroxypropyl)piperazin-1-yl)-N-((5-isobutyl-1-phenyl-1H-pyrazol-3-yl)methyl)acetamide (X=fluoro, R2=isobutyl, R3=H)

Yield: 83.0%, $^1$H-NMR (400 MHz, CDCl₃) δ=0.85-0.87 (6H, d, J=6.60 Hz, 2CH₃), 1.77-1.88 (1H, m, CH), 2.49-2.74 (12H, m, 6CH₂), 3.62 (2H, s, CH₂), 3.93-3.94 (2H, d, J=4.73 Hz, CH₂), 4.04-4.12 (1H, m, CH), 6.18 (1H, s, Ar), 6.84-6.88 (2H, m, 2Ph), 6.93-6.99 (2H, m, 2Ph), 7.35-7.39 (3H, m, 3Ph), 7.43-7.47 (2H, m, 2Ph)

KKRE10214

(S)-2-(4-(3-(4-Fluorophenoxy)-2-hydroxypropyl)piperazin-1-yl)-N-((5-isobutyl-1-phenyl-1H-pyrazol-3-yl)methyl)acetamide (X=fluoro, R2=isobutyl, R3=H)

Yield: 78.0%, $^1$H-NMR (400 MHz, CDCl₃) δ=0.86-0.87 (6H, d, J=6.62 Hz, 2CH₃), 1.77-1.87 (1H, m, CH), 2.48-2.74 (12H, m, 6CH₂), 3.62 (2H, s, CH₂), 3.93-3.94 (2H, d, J=4.40 Hz, CH₂), 4.04-4.11 (1H, m, CH), 6.18 (1H, s, Ar), 6.84-6.88 (2H, m, 2Ph), 6.92-6.98 (2H, m, 2Ph), 7.35-7.39 (3H, m, 3Ph), 7.43-7.47 (2H, m, 2Ph)

KKRE10215

(S)-2-(4-(2-Hydroxy-3-(4-(trifluoromethyl)phenoxy)propyl)piperazin-1-yl)-N-((5-isobutyl-1-phenyl-1H-pyrazol-3-yl)methyl)acetamide (X=trifluoromethyl, R2=isobutyl, R3=H)

Yield: 82.0%, $^1$H-NMR (400 MHz, CDCl₃) δ=0.86-0.87 (6H, d, J=6.60 Hz, 2CH₃), 1.77-1.88 (1H, m, CH), 2.50-2.51 (2H, d, J=7.12 Hz, CH₂), 2.53-2.75 (10H, m, 5CH₂), 3.62 (2H, s, CH₂), 4.01-4.02 (2H, m, CH₂), 4.07-4.13 (1H, m, CH), 6.18 (1H, s, Ar), 6.97-6.99 (2H, d, J=8.60 Hz, 2Ph), 7.37-7.39 (3H, m, 3Ph), 7.43-7.47 (2H, m, 2Ph), 7.52-7.54 (2H, d, J=8.65 Hz, 2Ph)

KKRE10216

(R)-N-((1-(5-fluoro-2-methylphenyl)-5-isobutyl-1H-pyrazol-3-yl)methyl)-2-(4-(2-hydoxy-3-(4-(trifluoromethyl)phenoxy)propyl)piperazin-1-yl)acetamide (X=trifluoromethyl, R2: isobutyl, R3=2-methyl-5-fluoro)

Yield: 91.0%, $^1$H-NMR (400 MHz, CDCl$_3$) δ=0.84-0.85 (6H, d, J=6.62 Hz, 2CH$_3$), 1.72-1.79 (1H, m, CH), 1.99 (3H, m, CH$_3$), 2.26-2.27 (2H, d, J=7.31 Hz, CH$_2$), 2.43-2.64 (10H, m, 5CH$_2$), 3.07 (2H, s, CH$_2$), 4.00-4.13 (3H, m, CH, CH$_2$), 4.50-4.51 (2H, d, J=5.72 Hz, CH$_2$), 6.13 (1H, s, Ar), 6.93-6.96 (1H, dd, J$_1$=8.67 Hz, J$_2$=2.65 Hz, Ph), 6.98-7.00 (2H, d, J=8.65 Hz, 2Ph), 7.06-7.11 (1H, td, J$_1$=8.28 Hz, J$_2$=2.68 Hz, Ph), 7.24-7.30 (1H, m, Ph), 7.54-7.56 (2H, d, J=8.64 Hz, 2Ph), 7.60-7.63 (1H, m, NH)

KKRE10217

(R)-N-((1-(4-fluorophenyl)-5-isobutyl-1H-pyrazol-3-yl)methyl)-2-(4-(2-hydroxy-3-(4-(trifluoromethyl)phenoxy)propyl)piperazin-1- yl)acetamide (X=trifluoromethyl, R2: isobutyl, R3=4-fluoro)

Yield: 94.0%, $^1$H-NMR (400 MHz, CDCl$_3$) δ=0.85-0.86 (6H, d, J=6.61 Hz, 2CH$_3$), 1.74-1.84 (1H, m, CH), 2.45-2.46 (2H, d, J=7.18 Hz, CH$_2$), 2.49-2.66 (10H, m, 5CH$_2$), 3.07 (2H, s, CH$_2$), 3.98-4.12 (3H, m, CH, CH$_2$), 4.50-4.51 (2H, d, J=5.70 Hz, CH$_2$), 6.10 (1H, s, Ar), 6.97-6.99 (2H, d, J=8.70 Hz, 2Ph), 7.13-7.18 (2H, m, 2Ph), 7.32-7.37 (2H, m, 2Ph), 7.53-7.55 (2H, d, J=8.74 Hz, 2Ph), 7.61-7.64 (1H, m, NH)

KKRE10218

(R)-N-((1-(3,5-dichlorophenyl)-5-isobutyl-1H-pyrazol-3-yl)methyl)-2-(4-(2-hydroxy-3-(4-(trifluoromethyl)phenoxy)propyl)piperazin-1- yl)acetamide (X=trifluoromethyl, R2: isobutyl, R3=3,5-dichloro)

Yield: 93.0%, $^1$H-NMR (400 MHz, CDCl$_3$) δ=0.89-0.91 (6H, d, J=6.59 Hz, 2CH$_3$), 1.80-1.90 (1H, m, CH), 2.50-2.70 (12H, m, 6CH$_2$), 3.08 (2H, s, CH$_2$), 4.01-4.02 (2H, d, J=4.50 Hz, CH$_2$), 4.06-4.12 (1H, m, CH), 4.49-4.51 (2H, d, J=5.56 Hz, CH$_2$), 6.15 (1H, s, Ar), 6.97-7.00 (2H, d, J=8.68 Hz, 2Ph), 7.33-7.39 (3H, m, 3Ph), 7.53-7.56 (2H, d, J=8.72 Hz, 2Ph), 7.72-7.74 (1H, m, NH)

KKRE10219

(S)-N-((1-(4-fluorophenyl)-5-isobutyl-1H-pyrazol-3-yl)methyl)-2-(4-(2-hydroxy-3-(4-(trifluoromethyl)phenoxy)propyl)piperazin-1- yl)acetamide (X=trifluoromethyl, R2: isobutyl, R3=4-fluoro)

Yield: 42.0%, $^1$H-NMR (400 MHz, CDCl$_3$) δ=0.85-0.86 (6H, d, J=6.60 Hz, 2CH$_3$), 1.74-1.84 (1H, m, CH), 2.45-2.47 (2H, d, J=7.14 Hz, CH$_2$), 2.49-2.66 (10H, m, 5CH$_2$), 3.07 (2H, s, CH$_2$), 3.98-4.12 (3H, m, CH, CH$_2$), 4.50-4.51 (2H, d, J=5.70 Hz, CH$_2$), 6.10 (1H, s, Ar), 6.97-6.99 (2H, d, J=8.66 Hz, 2Ph), 7.13-7.18 (2H, m, 2Ph), 7.33-7.37 (2H, m, 2Ph), 7.53-7.55 (2H, d, J=8.69 Hz, 2Ph), 7.61-7.64 (1H, m, NH)

KKRE10220

(S)-N-((1-(3,5-dichlorophenyl)-5-isobutyl-1H-pyrazol-3-yl)methyl)-2-(4-(2-hydroxy-3-(4-(trifluoromethyl)phenoxy)propyl)piperazin-1- yl)acetamide (X=trifluoromethyl, R2: isobutyl, R3=3,5-dichloro)

Yield: 82.0%, $^1$H-NMR (400 MHz, CDCl$_3$) δ+0.90-0.91 (6H, d, J=6.59 Hz, 2CH$_3$), 1.80-1.90 (1H, m, CH), 2.50-2.70 (12H, m, 6CH$_2$), 3.08 (2H, s, CH$_2$), 4.01-4.02 (2H, d, J=4.53 Hz, CH$_2$), 4.06-4.12 (1H, m, CH), 4.49-4.51 (2H, d, J=5.56 Hz, CH$_2$), 6.15 (1H, s, Ar), 6.97-7.00 (2H, d, J=8.70 Hz, 2Ph), 7.33-7.39 (3H, m, 3Ph), 7.53-7.56 (2H, d, J=8.76 Hz, 2Ph), 7.72-7.74 (1H, m, NH)

KKRE10221

(S)-N-((1-(5-fluoro-2-methylphenyl)-5-isobutyl-1H-pyrazol-3-yl)methyl)-2-(4-(2-hydroxy-3-(4-(trifluoromethyl)phenoxy)propyl)piperazin-1-yl)acetamide] (X=trifluoromethyl, R2: isobutyl, R3=2-methyl-5-fluoro)

Yield: 62.0%, $^1$H-NMR (400 MHz, CDCl$_3$) δ=0.84-0.85 (6H, d, J=6.63 Hz, 2CH$_3$), 1.72-1.79 (1H, m, CH), 1.99 (3H, m, CH$_3$), 2.26-2.28 (2H, d, J=7.28 Hz, CH$_2$), 2.44-2.64 (10H, m, 5CH$_2$), 3.07 (2H, s, CH$_2$), 4.00-4.13 (3H, m, CH, CH$_2$), 4.50-4.51 (2H, d, J=5.72 Hz, CH$_2$), 6.13 (1H, s, Ar), 6.93-6.96 (1H, dd, J$_1$=8.67 Hz, J$_2$=2.65 Hz, Ph), 6.98-7.00 (2H, d, J=8.60 Hz, 2Ph), 7.06-7.11 (1H, td, J$_1$=8.28 Hz, J$_2$=2.68 Hz, Ph), 7.24-7.30 (1H, m, Ph), 7.54-7.56 (2H, d, J=8.64 Hz, 2Ph), 7.60-7.63 (1H, m, NH)

KKRE10222

[(S)-2-(4-(2-Hydroxy-3-(4-(trifluoromethyl)phenoxy)propyl)piperazin-1-yl)-N-((5-isobutyl-1-o-tolyl-1H-pyrazol-3-yl)methyl)acetamide] (X=trifluoromethyl, R2: isobutyl, R3=2-methyl)

Yield: 57.0%, $^1$H-NMR (400 MHz, CDCl$_3$) δ=0.83-0.84 (6H, d, J=6.61 Hz, 2CH$_3$), 1.70-1.80 (1H, m, CH), 2.02 (3H, m, CH$_3$), 2.25-2.27 (2H, d, J=7.22 Hz, CH$_2$), 2.42-2.62 (10H, m, 5CH$_2$), 3.07 (2H, s, CH$_2$), 4.00-4.09 (3H, m, CH, CH$_2$), 4.51-4.52 (2H, d, J=5.67 Hz, CH$_2$), 6.11 (1H, s, Ar), 6.98-7.00 (2H, d, J=8.65 Hz, 2Ph), 7.18-7.20 (1 H, m, Ph), 7.27-7.37 (3H, m, 3Ph), 7.54-7.56 (2H, d, J=8.70 Hz, 2Ph), 7.60-7.63 (1H, m, NH)

KKRE10223

(R)-N-((1-(3,5-Dichlorophenyl)-5-isobutyl-1H-pyrazol-3-yl)methyl)-2-(4-(3-(4-fluorophenoxy)-2-hydroxypropyl)piperazin-1-yl)acetamide] (X=fluoro, R2: isobutyl, R3=3,5-dichloro)

Yield: 93.0%, $^1$H-NMR (400 MHz, CDCl$_3$) δ=0.89-0.91 (6H, d, J=6.61 Hz, 2CH$_3$), 1.80-1.90 (1H, m, CH), 2.48-2.70 (12H, m, 6CH$_2$), 3.08 (2H, s, CH$_2$), 3.93-3.94 (2H, d, J=4.82 Hz, CH$_2$), 4.03-4.08 (1H, m, CH), 4.49-4.51 (2H, d, J=5.70 Hz, CH$_2$), 6.15 (1H, s, Ar), 6.83-6.88 (2H, m, 2Ph), 6.94-7.00 (2H, m, 2Ph), 7.35 (2H, m, 2Ph), 7.37-7.38 (1H, m, Ph), 7.71-7.74 (1H, m, NH)

KKRE10224

(R)-N-((1-(5-Fluoro-2-methylphenyl)-5-isobutyl-1H-pyrazol-3-yl)methyl)-2-(4-(3-(4-fluorophenoxy)-2-hydroxypropyl)piperazin-1- yl)acetamide] (X=fluoro, R2: isobutyl, R3=2-methyl-5-fluoro)

Yield: 89.0%, $^1$H-NMR (400 MHz, CDCl$_3$) δ=0.83-0.85 (6H, d, J=6.58 Hz, 2CH$_3$), 1.71-1.82 (1H, m, CH), 2.26-2.28 (2H, d, J=7.23 Hz, CH$_2$), 2.42-2.62 (10H, m, 5CH$_2$), 3.06 (2H, s, CH$_2$), 3.92-3.94 (2H, d, J=4.71 Hz, CH$_2$), 4.00-4.06 (1H, m, CH), 4.50-4.51 (2H, d, J=5.70 Hz, CH$_2$), 6.12 (1H, s, Ar), 6.84-6.88 (2H, m, 2Ph), 6.93-6.99 (2H, m, 2Ph), 7.06-7.11 (1H, td, J$_1$=8.26 Hz, J$_2$=2.61 Hz, Ph), 7.26-7.29 (1H, m, Ph), 7.61-7.63 (1H, m, NH)

KKRE10225

(R)-2-(4-(3-(4-Fluorophenoxy)-2-hydroxypropyl)piperazin-1-yl)-N-((5-isobutyl-1-o-tolyl-1H-pyrazol-3-yl)methyl)acetamide] (X=fluoro, R2: isobutyl, R3=2-methyl)

Yield: 91.0%, $^1$H-NMR (400 MHz, CDCl$_3$) δ=0.82-0.84 (6H, d, J=6.60 Hz, 2CH$_3$), 1.70-1.80 (1H, m, CH), 2.01 (3H, s, CH$_3$), 2.24-2.26 (2H, d, J=7.22 Hz, CH$_2$), 2.41-2.61 (10H, m, 5CH$_2$), 3.06 (2H, s, CH$_2$), 3.92-3.94 (2H, d, J=4.77 Hz, CH$_2$), 3.99-4.05 (1H, m ,CH), 4.50-4.51 (2H, d, J=5.67 Hz, CH$_2$), 6.11 (1H, s, Ar), 6.84-6.87 (2H, m, 2Ph), 6.94-6.99 (2H, m, 2Ph), 7.17-7.19 (1H, d, J=7.59 Hz, Ph), 7.25-7.35 (3H, m, 3Ph), 7.62-7.63 (1H, m, NH)

KKRE10226

(R)-2-(4-(3-(4-Fluorophenoxy)-2-hydroxypropyl)piperazin-1-yl)-N-((1-(4-fluorophenyl)-5-isobutyl-1H-pyrazol-3-yl)methyl)acetamide] (X=fluoro, R2: isobutyl, R3=4-fluoro)

Yield: 92.0%, $^1$H-NMR (400 MHz, CDCl$_3$) δ=0.85-0.86 (6H, d, J=6.60 Hz, 2CH$_3$), 1.72-1.84 (1H, m, CH), 2.45-2.65 (12H, m, 6CH$_2$), 3.07 (2H, s, CH$_2$), 3.93-3.94 (2H, d, J=4.87 Hz, CH$_2$), 4.01-4.07 (1H, m, CH), 4.50-4.51 (2H, d, J=5.76 Hz, CH$_2$), 6.13 (1H, s, Ar), 6.84-6.87 (2H, m, 2Ph), 6.94-7.00 (2H, m, 2Ph), 7.13-7.18 (2H, m, 2Ph), 7.33-7.39 (3H, m, 3Ph), 7.62-7.64 (1H, m, NH)

KKRE10227

(S)-2-(4-(3-(4-Fluorophenoxy)-2-hydroxypropyl)piperazin-1-yl)-N-((5-isobutyl-1-o-tolyl-1H-pyrazol-3-yl)methyl)acetamide] (X=fluoro, R2: isobutyl, R3=2-methyl)

Yield: 86.0%, $^1$H-NMR (400 MHz, CDCl$_3$) δ=0.82-0.84 (6H, d, J=6.61 Hz, 2CH$_3$), 1.70-1.80 (1H, m, CH), 2.01 (3H, s, CH$_3$), 2.24-2.26 (2H, d, J=7.22 Hz, CH$_2$), 2.41-2.61 (10H, m, 5CH$_2$), 3.06 (2H, s, CH$_2$), 3.92-3.94 (2H, d, J=4.65 Hz, CH$_2$), 3.99-4.05 (1H, m, CH), 4.50-4.52 (2H, d, J=5.66 Hz, CH$_2$), 6.11 (1H, s, Ar), 6.84-6.88 (2H, m, 2Ph), 6.95-6.99 (2H, m, 2Ph), 7.18-7.20 (1H, d, J=7.58 Hz, Ph), 7.25-7.35 (3H, m, 3Ph), 7.61-7.62 (1H, m, NH)

KKRE10228

(S)-2-(4-(3-(4-Fluorophenoxy)-2-hydroxypropyl)piperazin-1-yl)-N-((1-(4-fluorophenyl)-5-isobutyl-1H-pyrazol-3-yl)methyl)acetamide] (X=fluoro, R2: isobutyl, R3=4-fluoro)

Yield: 42.0%, $^1$H-NMR (400 MHz, CDCl$_3$) δ=0.84-0.86 (6H, d, J=6.61 Hz, 2CH$_3$), 1.74-1.84 (1H, m, CH), 2.45-2.65 (12H, m, 6CH$_2$), 3.07 (2H, s, CH$_2$), 3.93-3.94 (2H, d, J=4.77 Hz, CH$_2$), 4.01-4.07 (1H, m, CH), 4.49-4.51 (2H, d, J=5.73 Hz, CH$_2$), 6.13 (1H, s, Ar), 6.84-6.87 (2H, m, 2Ph), 6.94-6.98 (2H, m, 2Ph), 7.13-7.18 (2H, m, 2Ph), 7.33-7.39 (3H, m, 3Ph), 7.61-7.64 (1H, m, NH)

KKRE10229

(S)-N-((1-(5-Fluoro-2-methylphenyl)-5-isobutyl-1H-pyrazol-3-yl)methyl)-2-(4-(3-(4-fluorophenoxy)-2-hydroxypropyl)piperazin-1- yl)acetamide] (X=fluoro, R2: isobutyl, R3=2-methyl-5-fluoro)

90.0%, $^1$H-NMR (400 MHz, CDCl$_3$) δ=0.83-0.85 (6H, d, J=6.60 Hz, 2CH$_3$), 1.70-1.82 (1H, m, CH), 2.26-2.27 (2H, d, J=7.24 Hz, CH$_2$), 2.42-2.62 (10H, m, 5CH$_2$), 3.06 (2H, s, CH$_2$), 3.92-3.94 (2H, d, J=4.42 Hz, CH$_2$), 4.00-4.06 (1H, m, CH), 4.49-4.51 (2H, d, J=5.70 Hz, CH$_2$), 6.11 (1H, s, Ar), 6.84-6.88 (2H, m, 2Ph), 6.93-6.99 (2H, m, 2Ph), 7.06-7.11 (1H, td, J$_1$=8.30 Hz, J$_2$=2.68 Hz, Ph), 7.26-7.29 (1H, m, Ph), 7.60-7.63 (1H, m, NH)

KKRE10230

(S)-N-((1-(3,5-Dichlorophenyl)-5-isobutyl-1H-pyrazol-3-yl)methyl)-2-(4-(3-(4-fluorophenoxy)-2-hydroxypropyl)piperazin-1-yl)acetamide] (X=fluoro, R2: isobutyl, R3=3,5-dichloro)

Yield: 95.0%, $^1$H-NMR (400 MHz, CDCl$_3$) δ=0.89-0.91 (6H, d, J=6.61 Hz, 2CH$_3$), 1.79-1.89 (1H, m, CH), 2.48-2.69 (12H, m, 6CH$_2$), 3.07 (2H, s, CH$_2$), 3.93-3.94 (2H, d, J=4.66 Hz, CH$_2$), 4.03-4.08 (1H, m, CH), 4.49-4.51 (2H, d, J=5.63 Hz, CH$_2$), 6.15 (1H, s, Ar), 6.84-6.88 (2H, m, 2Ph), 6.94-7.00 (2H, m, 2Ph), 7.34-7.35 (2H, m, 2Ph), 7.36-7.37 (1H, m, Ph), 7.71-7.74 (1H, m, NH)

Example 5

The phenoxypropanol derivative were prepared by the process indicated in reaction scheme 5.

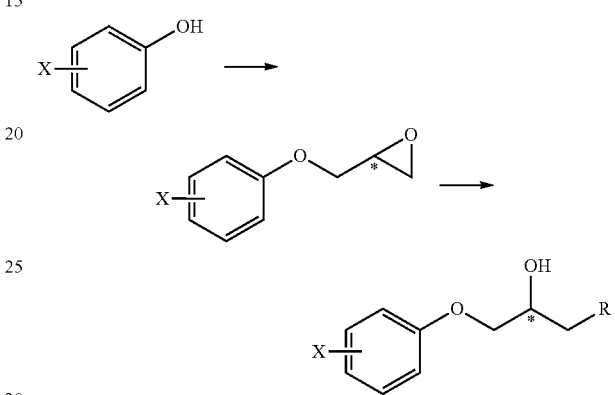

[Reaction Scheme 5]

1. (R) or (S)-epichlorohydrin, K$_2$CO$_3$, 2-butanone, reflux
2. 4-substituted piperidine deriveatives, i-PrOH, reflux, overnight (R)-2-(4-Fluoro-phenoxymethyl)oxirane (100 mg, 0.595 mmol) was dissolved in isopropyl alcohol 3 mL and was refluxed by heating for 18 hours with addition of morpholinopiperidine (131.61 mg, 0.773 mmol) in a dropwise. The obtained produce was concentrated under vacuum and the concentrated remaining produce was purified by a column chromatography (SiO$_2$, MC:MeOH=10:1 (v:v)) to produce a solid of (R)-1-(4-fluorophenoxy)-3-(4-morpholinopiperidin-1-yl)propan-2-ol (103.2 mg, Yield 75.40%).

KKRE10156

(R)-1-(4-fluorophenoxy)-3-(4-morpholinopiperidin-1-yl) propan-2-ol] (X=fluoro, R=Chemical Formula III, Y: 4-morpholino (4-morpholinopiperidinyl))

Yield: 75.40%, $^1$H-NMR (400 MHz, CDCl$_3$) δ=1.51-1.58 (m, 2H, CH$_2$), 1.85 (d, 2H, J=12.4 Hz, CH$_2$), 2.03 (t, 1H, J=11.72 Hz, CH$_a$), 2.16-2.20 (m, 1H, CH [piperidine]), 2.32 (t, J=11.72 Hz, CH$_b$), 2.43-2.51 (m, 2H, CH$_2$), 2.55 (t, 4H, J=4.66 Hz, 2CH$_2$ [morpholine]), 2.91 (d, 1H, J=12.84 Hz, CHCH$_a$), 3.07 (d, 1H, J=12.84 Hz, CHCH$_b$), 3.72 (t, 4H, J=4.71 Hz, 2CH$_2$ [morpholine]), 3.93 (d, 2H, J=4.8 Hz, OCH$_2$), 4.02-4.08 (m, 1H, CHOH), 6.85 (d, 1H, J=4.24 Hz, Ph), 6.87 (d, 1H, J=4.34 Hz, Ph), 6.96 (t, 2H, J=8.50 Hz, Ph)

In accordance with the same method as described above, oxiran compound ad piperidine compound having 2-(4-substituted oxymethyl)oxirane and N-(4-substituted benzyl)-2-(piperazin-1-yl)acetamide as R and X substituents were used for producing the following compounds:

R=morpholinopiperidinyl, piperidinopiperidinyl, 4,4-difluoropiperidinyl, pyrrolidinopiperidinyl, 4-hydroxy-4-phenylpiperidinyl, 3-methoxyphenylpiperidinyl, X=fluoro, trifluoromethyl

KKRE10157

(S)-1-(4-fluorophenoxy)-3-(4-morpholinopiperidin-1-yl)propan-2-ol] (X=fluoro, R=Chemical Formula III (Y=4-morpholino, 4-morpholinopiperidinyl))

Yield: 48.10%, $^1$H-NMR (400 MHz, CDCl$_3$) δ=1.51-1.58 (m, 2H, CH$_2$), 1.85 (d, 2H, J=12.4 Hz, CH$_2$), 2.03 (t, 1H, J=11.72 Hz, CH$_a$), 2.16-2.20 (m, 1H, CH [piperidine]), 2.32 (t, J=11.72 Hz, CH$_b$), 2.43-2.51 (m, 2H, CH$_2$), 2.55 (t, 4H, J=4.66 Hz, 2CH$_2$ [morpholine]), 2.91 (d, 1H, J=12.84 Hz, CHCH$_a$), 3.07 (d, 1H, J=12.84 Hz, CHCH$_b$), 3.72 (t, 4H, J=4.71 Hz, 2CH$_2$ [morpholine]), 3.93 (d, 2H, J=4.8 Hz, OCH$_2$), 4.02-4.08 (m, 1H, CHOH), 6.85 (d, 1H, J=4.24 Hz, Ph), 6.87 (d, 1H, J=4.34 Hz, Ph), 6.96 (t, 2H, J=8.50 Hz, Ph)

KKRE10158

(R)-1-(1,4'-bipiperidin-1'-yl)-3-(4-fluorophenoxy)propan-2-ol] (X=fluoro, R=Chemical Formula III (Y=4-piperidino, 4-piperidinopiperidinyl))

Yield: 48.2%, $^1$H-NMR (400 MHz, CDCl$_3$) δ=1.52-1.66 (m, 8H, 4CH$_2$), 1.99 (t, 2H, J=11.56 Hz, 2CH), 2.43-2.55 (m, 8H, 4CH$_2$), 2.91 (d, 1H, J=10.74 Hz, CHCH$_a$), 3.07 (d, 1H, J=11.24 Hz, CHCH$_b$), 3.93 (d, 2H, J=4.84 Hz, OCH$_2$), 4.03-4.06 (m, 1H, CHOH), 6.86 (dd, J$_1$=9.12 Hz, J$_2$=4.3 Hz, Ph), 6.96 (t, 2H, J=8.32 Hz, Ph)

KKRE10159

(S)-1-(1,4'-bipiperidin-1'-yl)-3-(4-fluorophenoxy)propan-2-ol] (X=fluoro, R=Chemical Formula III (Y=4-piperidino, 4-piperidinopiperidinyl))

Yield: 75.26%, $^1$H-NMR (400 MHz, CDCl$_3$) δ=1.52-1.66 (m, 8H, 4CH$_2$), 1.99 (t, 2H, J=11.56 Hz, 2CH), 2.43-2.55 (m, 8H, 4CH$_2$), 2.91 (d, 1H, J=10.74 Hz, CHCH$_a$), 3.07 (d, 1H, J=11.24 Hz, CHCH$_b$), 3.93 (d, 2H, J=4.84 Hz, OCH$_2$), 4.03-4.06 (m, 1H, CHOH), 6.86 (dd, J$_1$=9.12 Hz, J$_2$=4.3 Hz, Ph), 6.96 (t, 2H, J=8.32 Hz, Ph)

KKRE10160

(R)-1-(4-fluorophenoxy)-3-(4-(pyrrolidin-1-yl)piperidin-1-yl)propan-2-ol] (X=fluoro, R=Chemical Formula III (Y=4-pyrrolidino, 4-pyrrolidinopiperidinyl))

Yield: 84.96%, $^1$H-NMR (400 MHz, CDCl$_3$) δ=1.54-1.67 (m, 2H, CH$_2$), 1.78-1.81 (m, 4H, 2CH$_2$), 1.92 (d, 2H, J=12.87 Hz, CH$_2$), 1.99-2.08 (m, 2H, CH$_2$), 2.35 (td, 1H, J$_1$=11.74 Hz, J$_2$=2.22 Hz, CH), 2.46-2.50 (m, 2H, CH$_2$), 2.53-2.59 (m, 4H, 2CH$_2$), 2.86, (d, 1H, J=12.53 Hz, CHCH$_a$), 3.02 (d, 1H, J=12.80 Hz, CHCH$_b$), 3.93 (d, 1H, J=4.80 Hz, CH$_2$), 4.03-4.07 (m, 1H, CHOH), 6.86 (dd, J$_1$=9.12 Hz, J$_2$=4.3 Hz, Ph), 6.98 (t, 2H, J=8.32 Hz, Ph)

KKRE10161

(S)-1-(4-fluorophenoxy)-3-(4-(pyrrolidin-1-yl)piperidin-1-yl)propan-2-ol] (X=fluoro, R=Chemical Formula III (Y=4-pyrrolidino, 4-pyrrolidinopiperidinyl))

Yield: 48.2%, $^1$H-NMR (400 MHz, CDCl$_3$) δ=1.54-1.67 (m, 2H, CH$_2$), 1.78-1.81 (m, 4H, 2CH$_2$), 1.92 (d, 2H, J=12.87 Hz, CH$_2$), 1.99-2.08 (m, 2H, CH$_2$), 2.35 (td, 1H, J$_1$=11.74 Hz, J$_2$=2.22 Hz, CH), 2.46-2.50 (m, 2H, CH$_2$), 2.53-2.59 (m, 4H, 2CH$_2$), 2.86, (d, 1H, J=12.53 Hz, CHCH$_a$), 3.02 (d, 1H, J=12.80 Hz, CHCH$_b$), 3.93 (d, 1H, J=4.80 Hz, CH$_2$), 4.03-4.07 (m, 1H, CHOH), 6.86 (dd, J$_1$=9.12 Hz, J$_2$=4.3 Hz, Ph), 6.98 (t, 2H, J=8.32 Hz, Ph)

KKRE10162

(R)-1-(4-fluorophenoxy)-3-(4-(3-methoxyphenyl)piperidin-1-yl)propan-2-ol] (X=fluoro, R=Chemical Formula III (Y=3-methoxyphenyl, 3-methoxyphenyl piperidine))

Yield: 32.79%

$^1$H NMR (400 MHz, CDCl$_3$) δ=1.73-1.88 (m, 4H, 2CH$_2$ (piperidine)), 2.12 (td, 1H, J$_1$=11.6 Hz, J$_2$=2.13 Hz), 2.40-2.61 (m, 4H, 2CH$_2$(piperidine)), 2.97 (d, 1H, CH$_a$, J=12.4 Hz), 3.14 (d, 1H, CH$_b$, J=10.4 Hz), 3.81 (s, 3H, OMe), 3.97 (d, 2H, CH$_2$, J=4.84 Hz), 4.09-4.12 (m, 1H, CH), 6.74-7.23 (m, 8H, 2Ph)

KKRE10163

(S)-1-(4-fluorophenoxy)-3-(4-(3-methoxyphenyl)piperidin-1-yl)propan-2-ol] (X=fluoro, R=Chemical Formula III (Y=3-methoxypheny, 3-methoxyphenyl piperidine))

Yield: 25.19%

$^1$H NMR (400 MHz, CDCl$_3$) δ=1.70-1.88 (m, 4H, 2CH$_2$ [piperidine]), 2.13 (td, 1H, J$_1$=11.7 Hz, J$_2$=2.13 Hz), 2.41-2.62 (m, 4H, 2CH$_2$[piperidine]), 2.97 (d, 1H, CH$_a$, J=11.6 Hz), 3.14 (d, 1H, CH$_b$, J=11.2 Hz), 3.81 (s, 3H, OMe), 3.97 (d, 2H, CH$_2$, J=5.2 Hz), 4.09-4.12 (m, 1H, CH), 6.75-7.23 (m, 8H, 2Ph)

KKRE10178

(R)-1-(4,4-difluoropiperidin-1-yl)-3-(4-fluorophenoxy)propan-2-ol] (X=fluoro, R=Chemical Formula III (Y=4,4-difluoro, 4,4-difluoropiperidine))

Yield: 37.08%, $^1$H-NMR (400 MHz, CDCl$_3$) δ=1.98-2.08 (m, 4H, 2CH$_2$), 2.55-2.65 (m, 4H, 2CH$_2$), 2.75-2.81 (m, 2H, CH$_2$), 3.94 (d, 1H, CHa), 3.95 (s, 1H, CHb), 4.05-4.09 (m, 1H, CHOH), 6.86 (dd, J$_1$=9.14 Hz, J$_2$=4.33 Hz, Ph), 6.97 (t, 2H, J=9.06 Hz, Ph)

KKRE10179

(R)-4-fluoro-1-(3-(4-fluorophenoxy)-2-hydroxypropyl)piperidin-4-ol (X=fluoro, R=Chemical Formula III (Y=4-hydroxy-4-phenyl, 4-hydroxy-4-phenyl piperidine))

Yield: 67.06%, $^1$H-NMR (400 MHz, CDCl$_3$) δ=1.80 (d, 2H, J=11.82 Hz, CH$_2$), 2.09-2.23 (m, 2H, CH$_2$), 2.54 (td, 1H, J$_1$=11.70 Hz, J$_2$=2.20 Hz, CH$_a$), 2.60-2.62 (m, 2H, CH$_2$), 2.76 (d, 1H, J=11.30 Hz, CH$_{a'}$), 2.84 (td, 1H, J$_1$=11.70 Hz, J$_2$=2.20 Hz, CH$_b$), 2.93 (d, 1H, J=11.30 Hz, CH$_{b'}$), 3.98 (d, 2H, J=4.48 Hz, CH$_2$), 4.10-4.14 (m, 1H, CHOH), 6.88 (dd, J$_1$=9.12 Hz, J$_2$=4.33 Hz, Ph), 6.97 (t, 2H, J=8.41 Hz, Ph), 7.29 (d, J=7.3 Hz, Ph), 7.38 (t, 2H, J=7.88 Hz, Ph), 7.52 (d, 2H, J=7.62 Hz, Ph)

KKRE10180

(S)-1-(4,4-difluoropiperidin-1-yl)-3-(4-fluorophenoxy)propan-2-ol] (X=fluoro, R=Chemical Formula III (Y=4,4-difluoro, 4,4-difluoropiperidine))

Yield: 29.82%, $^1$H-NMR (400 MHz, CDCl$_3$) δ=1.98-2.08 (m, 4H, 2CH$_2$), 2.55-2.65 (m, 4H, 2CH$_2$), 2.75-2.81 (m, 2H, CH$_2$), 3.94 (d, 1H, CHa), 3.95 (s, 1H, CHb), 4.05-4.09 (m, 1H, CHOH), 6.86 (dd, J$_1$=9.14 Hz, J$_2$=4.33 Hz, Ph), 6.97 (t, 2H, J=9.06 Hz, Ph)

KKRE10181

(S)-4-fluoro-1-(3-(4-fluorophenoxy)-2-hydroxyppropyl)piperidin-4-ol (X=fluoro, R=Chemical Formula III (Y=4-hydroxy-4-phenyl, 4-hydroxy-4-phenyl piperidine))

Yield: 81.63%, $^1$H-NMR (400 MHz, CDCl$_3$) δ=1.80 (d, 2H, J=11.82 Hz, CH$_2$), 2.09-2.23 (m, 2H, CH$_2$), 2.54 (td, 1H, J$_1$=11.70 Hz, J$_2$=2.20 Hz, CH$_a$), 2.60-2.62 (m, 2H, CH$_2$), 2.76 (d, 1H, J=11.30 Hz, CH$_a$), 2.84 (td, 1H, J$_1$=11.70 Hz, J$_2$=2.20 Hz, CH$_b$), 2.93 (d, 1H, J=11.30 Hz, CH$_b$'), 3.98 (d, 2H, J=4.48 Hz, CH$_2$), 4.10-4.14 (m, CHOH), 6.88 (dd, J$_1$=9.12 Hz, J$_2$=4.33 Hz, Ph), 6.97 (t, 2H, J=8.41 Hz, Ph), 7.29 (d, J=7.3 Hz, Ph), 7.38 (t, 2H, J=7.88 Hz, Ph), 7.52 (d, 2H, J=7.62 Hz, Ph)

KKRE10182

(R)-1-(4-morpholinopiperidin-1-yl)-3-(4-(trifluoromethyl)phenoxy)propan-2-ol] (X=trifluoromethyl, R=Chemical Formula III (Y=4-morpholino, 4-morpholinopiperidinyl))

Yield: 33.7%, $^1$H-NMR (400 MHz, CDCl$_3$) δ=1.49-1.59 (m, 2H, CH$_2$), 1.87 (d, 2H, J=12.08 Hz, CH$_2$), 2.02 (t, 1H, J=10.16 Hz, CH$_a$), 2.17-2.20 (m, 1H, CH [piperidine]), 2.34 (t, J=11.60 Hz, CH$_b$), 2.47-2.51 (m, 2H, CH$_2$), 2.54 (t, 4H, J=5.50 Hz, 2CH$_2$ [morpholine]), 2.92 (d, 1H, J=11.12 Hz, CHCH$_a$), 3.07 (d, 1H, J=10.96 Hz, CHCH$_b$), 3.73 (t, 4H, J=4.56 Hz, 2CH$_2$ [morpholine]), 4.02 (d, 2H, J=4.78 Hz, OCH$_2$), 4.06-4.19 (m, 1H, CHOH), 6.98 (d, 1H, J=8.82 Hz, Ph), 7.54 (d, 1H, J=8.82 Hz, Ph)

KKRE10183

(R)-1-(1,4'-bipiperidin-1'-yl)-3-(4-(trifluoromethyl)phenoxy)propan-2-ol] (X=trifluoromethyl, R=Chemical Formula III (Y=4-piperino, 4-piperidinopiperidinyl))

Yield: 25.09%, $^1$H-NMR (400 MHz, CDCl$_3$) δ=1.51-1.66 (m, 3H, CH$_2$+CH), 1.80, (brs, 4H, 2CH$_2$), 1.92 (d, 2H, J=12.77 Hz, CH$_2$), 2.06 (t, 2H, J=11.70 Hz, CH$_2$), 2.36 (t, 2H, J=11.78 Hz, CH$_2$), 2.45-2.55 (m, 2H, CH$_2$), 2.59 (brs, 4H, 2CH$_2$), 2.85 (d, 1H, J=11.54 Hz, CHCH$_a$), 3.03 (d, 1H, J=11.27 Hz, CHCH$_b$), 3.92 (d, 2H, J=4.95 Hz, OCH$_2$), 4.01-4.11 (m, 1H, CHOH), 6.99 (dd, J=8.75 Hz), 7.54 (d, 2H, J=8.75 Hz, Ph)

KKRE10184

(R)-1-(4-(pyrrolidin-1-yl)piperidin-1-yl)-3-(4-(trifluoromethyl)phenoxy)propan-2-ol] (X=trifluoromethyl, R=Chemical Formula III (Y=4-pyrrolidinopiperidinyl, 4-pyrrolidinopiperidinyl))

Yield: 39.60%, $^1$H-NMR (400 MHz, CDCl$_3$) δ=1.44-1.47 (m, 2H, CH$_2$), 1.56-1.63 (m, 5H, 2CH$_2$+CH$_a$), 1.82 (d, 2H, J=10.32 Hz, CH$_2$), 2.00-2.05 (m, 1H, CH), 2.26-2.32 (m, 2H, CH$_2$), 2.45-2.58 (m, 5H, 2CH$_2$+CH$_b$), 2.90, (d, 1H, J=11.88 Hz, CHCH$_a$), 3.08 (d, 1H, J=11.40 Hz, CHCH$_b$), 3.99 (d, 1H, J=4.74 Hz, CH$_2$), 4.04-4.09 (m, 1H, CHOH), 6.98 (d, J=8.7 Hz, Ph), 7.54 (d, 2H, J=8.7 Hz, Ph)

KKRE10185

(R)-1-(4,4-difluoropiperidin-1-yl)-3-(4-(trifluoromethyl)phenoxy)propan-2-ol] (X=trifluoromethyl, R=Chemical Formula III (Y=4,4-difluo(4,4-difluoropiperidinyl))

Yield: 49.06%, $^1$H-NMR (400 MHz, CDCl$_3$) δ=1.98-2.08 (m, 4H, 2CH$_2$), 2.55-2.65 (m, 4H, 2CH$_2$), 2.75-2.81 (m, 2H, CH$_2$), 3.94 (d, 1H, CHa), 3.95 (s, 1H, CHb), 4.39-4.45 (m, 1H, CHOH), 6.99 (d, J=8.49 Hz, Ph), 7.24 (d, 2H, J=8.72 Hz, Ph)

KKRE10186

(R)-1-(2-hydroxy-3-(4-(trifluoromethyl)phenoxy)propyl)-4-phenylpiperidin-4-ol] (X=trifluoromethyl, R=Chemical Formula III (Y=4-hydroxy-4-phenoxy, 4-hydroxy-4-phenoxypiperidine))

Yield: 28.08%, $^1$H-NMR (400 MHz, CDCl$_3$) δ=1.82 (d, 2H, J=11.72 Hz, CH$_2$), 2.10-2.24 (m, 2H, CH$_2$), 2.57 (d, 1H, J=11.16 Hz, CH$_a$), 2.62-2.64 (m, 2H, CH$_2$), 2.77 (d, 1H, J=9.88 Hz, CH$_a$'), 2.85 (d, 1H, J=11.76 Hz, CH$_b$), 2.93 (d, 1H, J=11.07 Hz, CH$_b$'), 4.05 (m, 2H, CH$_2$), 4.13-4.19 (m, 1H, CHOH), 7.01 (d, 2H, J=8.54 Hz, Ph), 7.29 (t, 2H, 1H, J=7.46 Hz, Ph), 7.38 (t, 2H, J=7.94 Hz, Ph), 7.49-7.58 (m, 4H, Ph)

KKRE10187

(S)-1-(4-morpholinopiperidin-1-yl)-3-(4-(trifluoromethyl)phenoxy)propan-2-ol] (X=trifluoromethyl, R=Chemical Formula III (Y=4-morpholino, 4-morpholinopiperidinyl))

Yield: 38.25%, $^1$H-NMR (400 MHz, CDCl$_3$) δ=1.49-1.59 (m, 2H, CH$_2$), 1.87 (d, 2H, J=12.08 Hz, CH$_2$), 2.02 (t, 1H, J=10.16 Hz, CH$_a$), 2.17-2.20 (m, 1H, CH [piperidine]), 2.34 (t, J=11.60 Hz, CH$_b$), 2.47-2.51 (m, 2H, CH$_2$), 2.54 (t, 4H, J=5.50 Hz, 2CH$_2$ [morpholine]), 2.92 (d, 1H, J=11.12 Hz, CHCH$_a$), 3.07 (d, 1H, J=10.96 Hz, CHCH$_b$), 3.73 (t, 4H, J=4.56 Hz, 2CH$_2$ [morpholine]), 4.02 (d, 2H, J=4.78 Hz, OCH$_2$), 4.06-4.19 (m, 1H, CHOH), 6.98 (d, 1H, J=8.82 Hz, Ph), 7.54 (d, 1H, J=8.82 Hz, Ph)

KKRE10188

(S)-1-(1,4'-bipiperidin-1'-yl)-3-(4-(trifluoromethyl)phenoxy)propan-2-ol] (X=trifluoromethyl, R=Chemical Formula III (Y=4-piperidino, 4-piperidinopiperidine))

Yield: 51.21%, $^1$H-NMR (400 MHz, CDCl$_3$) δ=1.51-1.66 (m, 3H, CH$_2$+CH), 1.80, (brs, 4H, 2CH$_2$), 1.92 (d, 2H, J=12.77 Hz, CH$_2$), 2.06 (t, 2H, J=11.70 Hz, CH$_2$), 2.36 (t, 2H, J=11.78 Hz, CH$_2$), 2.45-2.55 (m, 2H, CH$_2$), 2.59 (brs, 4H, 2CH$_2$), 2.85 (d, 1H, J=11.54 Hz, CHCH$_a$), 3.03 (d, 1H, J=11.27 Hz, CHCH$_b$), 3.92 (d, 2H, J=4.95 Hz, OCH$_2$), 4.01-4.11 (m, 1H, CHOH), 6.99 (dd, J=8.75 Hz), 7.54 (d, 2H, J=8.75 Hz, Ph)

KKRE10189

(S)-1-(4-(pyrrolidin-1-yl)piperidin-1-yl)-3-(4-(trifluoromethyl)phenoxy)propan-2-ol] (X=trifluoromethyl, R=Chemical Formula III (Y=4-pyrrolidino, 4-pyrrolidinopiperidine))

Yield: 42.88%, $^1$H-NMR (400 MHz, CDCl$_3$) δ=1.44-1.47 (m, 2H, CH$_2$), 1.56-1.63 (m, 5H, 2CH$_2$+CH$_a$), 1.82 (d, 2H, J=10.32 Hz, CH$_2$), 2.00-2.05 (m, 1H, CH), 2.26-2.32 (m, 2H, CH$_2$), 2.45-2.58 (m, 5H, 2CH$_2$+CH$_b$), 2.90, (d, 1H, J=11.88 Hz, CHCH$_a$), 3.08 (d, 1H, J=11.40 Hz, CHCH$_b$), 3.99 (d, 1H, J=4.74 Hz, CH$_2$), 4.04-4.09 (m, 1H, CHOH), 6.98 (d, J=8.7 Hz, Ph), 7.54 (d, 2H, J=8.7 Hz, Ph)

KKRE10190

(S)-1-(4,4-difluoropiperidin-1-yl)-3-(4-(trifluoromethyl)phenoxy)propan-2-ol] (X=trifluoromethyl, R=Chemical Formula III (Y=4,4-difluoro, 4,4-difluoropiperidine))

Yield: 15.10%, $^1$H-NMR (400 MHz, CDCl$_3$) δ=1.98-2.08 (m, 4H, 2CH$_2$), 2.55-2.65 (m, 4H, 2CH$_2$), 2.75-2.81 (m, 2H, CH$_2$), 3.94 (d, 1H, CHa), 3.95 (s, 1H, CHb), 4.39-4.45 (m, 1H, CHOH), 6.99 (d, J=8.49 Hz, Ph), 7.24 (d, 2H, J=8.72 Hz, Ph)

KKRE10191

(S)-1-(2-hydroxy-3-(4-(trifluoromethyl)phenoxy)propyl)-4-phenylpiperidin-4-ol] (X=trifluoromethyl, R=Chemical Formula III (Y=hydroxyphenoxy, 4-hydroxy-4-phenoxypiperidine))

Yield: 86.07%, $^1$H-NMR (400 MHz, CDCl$_3$) δ=1.82 (d, 2H, J=11.72 Hz, CH$_2$), 2.10-2.24 (m, 2H, CH$_2$), 2.57 (d, 1H, J=11.16 Hz, CH$_a$), 2.62-2.64 (m, 2H, CH$_2$), 2.77 (d, 1H, J=9.88 Hz, CH$_a$'), 2.85 (d, 1H, J=11.76 Hz, CH$_b$), 2.93 (d, 1H, J=11.07 Hz, CH$_b$'), 4.05 (m, 2H, CH$_2$), 4.13-4.19 (m, 1H, CHOH), 7.01 (d, 2H, J=8.54 Hz, Ph), 7.29 (t, 2H, 1H, J=7.46 Hz, Ph), 7.38 (t, 2H, J=7.94 Hz, Ph), 7.49-7.58 (m, 4H, Ph)

Experimental Example 1

Assay for T-type Calcium Channel Inhibition Activity

At 12-24 hours before the assay for T-type calcium channel activity, cells of HEK293 cell line (α1G cell line: KCTC 10519BP, GenBank, Korea Research Institute of Bioscience and Biotechnology) which stably express α1G T-type calcium channel and Kir2.1, were sub-cultured in a poly-L-lysine (0.05 mg/ml) treated 96-well plate with the density of $4 \times 10^4$ per a well using a 96-well cell dispenser (Titertek). On the day of assay, the 96-well plate to which the cells were attached were washed three times with a HEPES buffer solution (unit mM: 150 NaCl, 5 KCl, 1 $MgCl_2$, 2 $CaCl_2$, 10 HEPES, 10 glucose, pH 7.4) using a 96-well plate automatic washing device (Bio Tek), and then reacted with a HEPES buffer solution containing 5 µM fluo-3/AM and 0.001% (w/v) Pluronic F-127 at room temperature for 1 hour, to label with fluorescent dye, and then further washed twice with the HEPES buffer solution. Thereafter, at 10 minutes before the measurement using a FDSS6000 device, a washing with a HEPES buffer solution containing 10 mM $CaCl_2$ was conducted once more, and the final volume was adjusted to 81 µl. Besides the above 96-well plate containing the cells, additional two 96-well drug plates were provided, in which the 96-well plates contained KCl (final concentration: 75 mM) for activating T-type calcium channel and a blocker drug, respectively.

Since most of cell-based HTS (High throughput screening) devices are equipped with a liquid application system for drug injection, but have no liquid sucking system, the blocker drug to be tested and KCl were respectively provided at the five-times higher concentration in 10 mM $CaCl_2$ HEPES buffer solution at the amount of 27 µl, diluted five-times at the final cell plate volume of 135 µl, and then used in this test. In this Experimental Example, therefore, FDSS6000 (Hamamatsu Photonics) was used as an alternative to HTS device.

Specific FDSS6000 measurement conditions are as follows: After recording the reference value of 20 seconds, the change of intracellular calcium concentration which induced by pre-treatment of the drug (the prepared compound, 10 mM) for 75 seconds followed by administration of KCl was measured, in which the percentage (%) inhibition effect of the test drug was determined, through estimating the area of ratio value of 340/380 in the control without treatment of the test drug as 100%. As a reference drug, 10 µM of mibefradil was always used.

For accurate calcium-imagination, the light sources of 4 xenon lamps in FDSS6000 were radiated to make the cells exposed selectively to the excitation wavelength (340 nm and 380 nm) by computer-controlled filter wheel. Data was obtained at interval of each 1.23 second. The emitter fluorescence light inflow through a 515 nm long-pass filter was obtained as an average 340/380 ratio value for each well in the 96-wells by a cooled CCD camera and digital fluorescence analyzer in the device. All image data and analysis were obtained by using a FDSS6000-exclusive program provided by Hamamatsu Photonics, as described above.

TABLE 1

Inhibition activity of the prepared compounds against T-type calcium channel

| code | calcium channel activity (% inhibition/FDSS/10 mM) |
| --- | --- |
| KKRE10153 | 46.86 |
| KKRE10154 | 39.90 |
| KKRE10155 | 33.69 |
| KKRE10196 | 26.03 |
| KKRE10197 | 27.11 |
| KKRE10198 | 28.60 |
| KKRE10199 | 33.92 |
| KKRE10200 | 43.74 |
| KKRE10201 | 55.41 |
| KKRE10202 | 21.43 |
| KKRE10203 | 17.04 |
| KKRE10204 | 12.28 |
| KKRE10173 | 53.65 |
| KKRE10174 | 48.84 |
| KKRE10175 | 43.10 |
| KKRE10176 | 43.89 |
| KKRE10177 | 41.95 |
| KKRE10211 | 79.03 |
| KKRE10212 | 74.31 |
| KKRE10210 | 66.97 |
| KKRE10213 | 77.40 |
| KKRE10214 | 77.49 |
| KKRE10215 | 80.86 |
| KKRE10216 | 77.41 |
| KKRE10217 | 75.74 |
| KKRE10218 | 73.52 |
| KKRE10219 | 74.07 |
| KKRE10220 | 35.75 |
| KKRE10221 | 68.90 |
| KKRE10222 | 79.16 |
| KKRE10223 | 63.40 |
| KKRE10224 | 77.76 |
| KKRE10225 | 81.07 |
| KKRE10226 | 78.82 |
| KKRE10227 | 74.74 |
| KKRE10228 | 73.20 |
| KKRE10229 | 77.56 |
| KKRE10230 | 59.98 |
| KKRE10156 | 5.31 |
| KKRE10157 | 9.33 |
| KKRE10158 | 6.65 |
| KKRE10159 | 6.37 |
| KKRE10160 | 0.31 |
| KKRE10161 | −0.06 |
| KKRE10178 | 37.57 |
| KKRE10179 | 15.99 |
| KKRE10180 | 17.26 |
| KKRE10181 | 35.38 |
| KKRE10182 | 12.54 |
| KKRE10183 | 11.96 |
| KKRE10184 | 9.54 |
| KKRE10185 | 14.78 |
| KKRE10186 | 46.14 |
| KKRE10187 | 10.11 |
| KKRE10188 | 5.73 |
| KKRE10189 | 8.45 |
| KKRE10190 | 34.95 |
| KKRE10191 | 16.78 |

Experimental Example 2

Assay for TREK Channel Inhibition Activity

The inhibition activity of the compound of the present invention against TREK-1 channel was measured by measuring the physiological activity by whole cell patch clamp recording.

COS7 cell (obtained from Korean Cell Line Bank (KCLB)) was transfected with GFP-rTREK-1 gene (accession number: AY727922) using an Effectene transfection reagent (Qiagen), and cultured for 24 hours in an incubator at 37° C. As a culture medium, Dulbecco's modified Eagle's medium (DMEM, GIBCO products from Invitrogen) containing 10% by weight of fetal bovine serum (FBS) and 1% by weight of penicillin/streptomycin (5000 unit/ml) was used. The cells thus prepared were adhered on a cover glass, which was placed on a chamber, and then a recording solution (150 mM NaCl, 10 mM HEPES, 10 mM KCl, 2 mM CaCl$_2$, 5.5 mM D-Glucose, all reagents were purchased from Sigma) was applied. A glass microelectrode was filled with an intracellular solution prepared with the composition of 150 mM KCl, 5 mM EGTA, 10 mM HEPES, 0.5 mM CaCl$_2$, 1 mM MgCl$_2$, 4 mM Mg-ATP, and 0.3 mM Na-GTP (all reagents were purchased from Sigma), followed by whole-cell patch clamp recording. The voltage was fixed at −70 mV using a Digidata 1322A data acquisition system (Molecular Devices) and an Axopatch 200A amplifier (Axon Instruments), and the current generated by applying a voltage ramp from −100 mV to +100 mV for 1 second was measured using a Clampex9.2 program. A difference between the current values measured at +100 mV and −100 mV was defined as a current in the above experiment. The currents before and after blocker treatment were measured so as to determine the inhibition activity.

Block %=100−(current after blocker treatment/current before blocker treatment)*100

The inhibition activity against TREK-1 channel thus obtained is shown in the following Tables 2 and 3.

TABLE 2

| Name | Structure | M.W | block % at 100 μM | n | block % at 10 μM | n |
|---|---|---|---|---|---|---|
| quinine | | 324.42 | 50.00 | 5 | 17.00 | 5 |
| quinidine | | 324.42 | 33.46 | 2 | | |
| hydroquinine | | 326.43 | 49.71 | 5 | 19.84 | 5 |
| KKRE10138 | 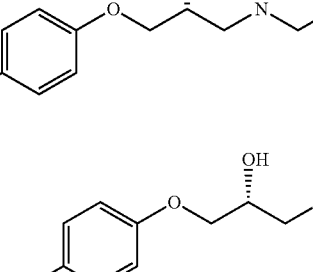 | 392.89 | 71.47 | 5 | 12.97 | 4 |
| KKRE10145 | 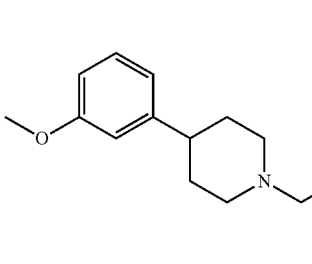 | 455.45 | | | 35.24 | 5 |
| KKRE10153 | 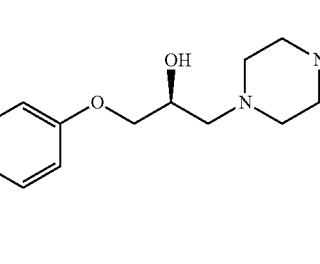 | 474.52 | | | 52.07 | 5 |
| KKRE10162 | 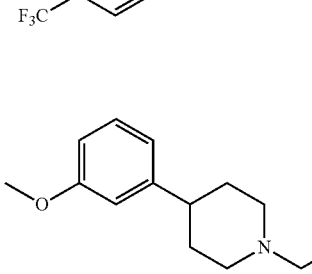 | 359.43 | | | 52.52 | 6 |
| KKRE10174 | 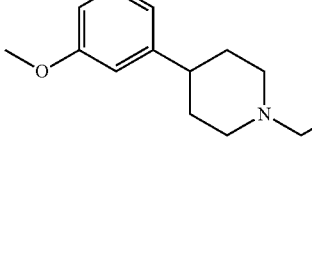 | 519.48 | 88.17 | 6 | 37.63 | 5 |

TABLE 2-continued
| Name | Structure | M.W | block % at 100 μM | n | block % at 10 μM | n |
|---|---|---|---|---|---|---|
| KKRE10175 | 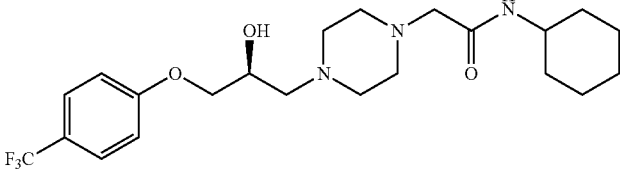 | 465.51 | 74.61 | 5 | 18.10 | 4 |
| KKRE10210 | 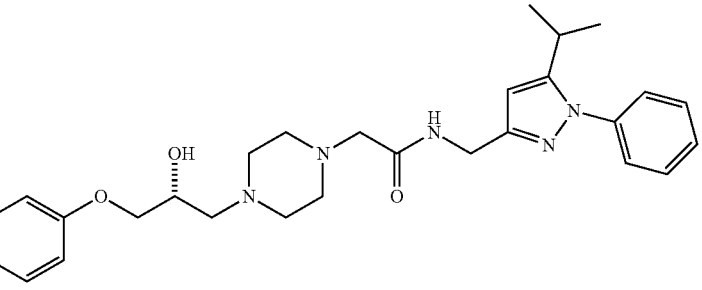 | 573.65 | 91.23 | 5 | | |
| KKRE10213 | 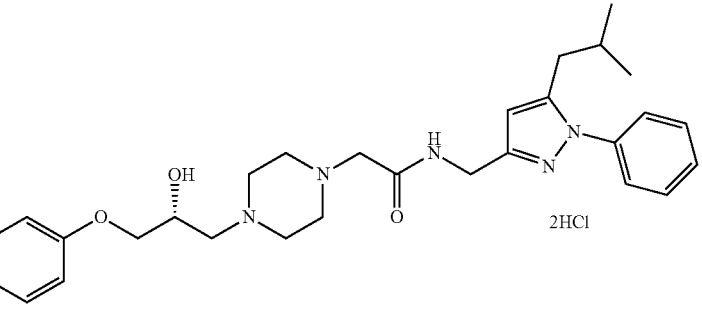 | 596.56 | | | 64.67 | 4 |
| KKRE10173 | 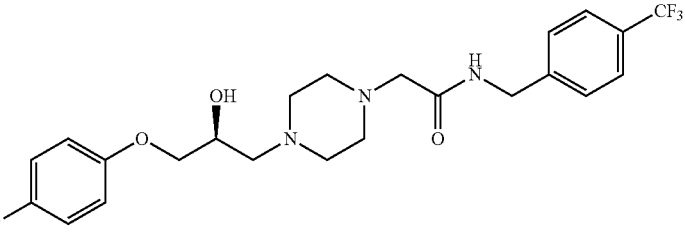 | 348.48 | | | 63.20 | 5 |
| KKRE10174 | 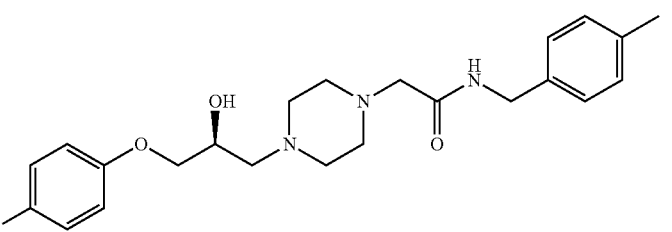 | 519.48 | | | 35.60 | 7 |
| KKRE10198 | 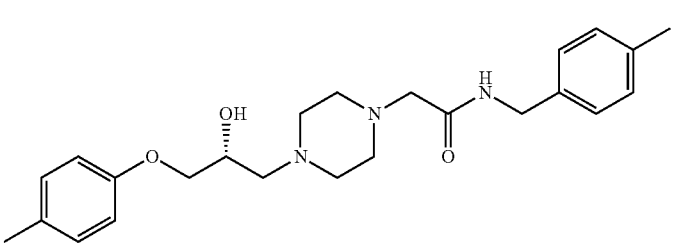 | 411.54 | | | 29.86 | 5 |

TABLE 2-continued

| Name | Structure | M.W | block % at 100 μM | n | block % at 10 μM | n |
|---|---|---|---|---|---|---|
| KKRE10200 | 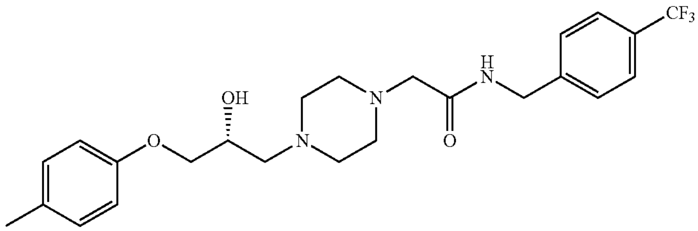 [SMILES: Cc1ccc(OC[C@H](O)CN2CCN(CC(=O)NCc3ccc(C(F)(F)F)cc3)CC2)cc1] | 465.51 | | | 30.94 | 5 |
| KKRE10201 | 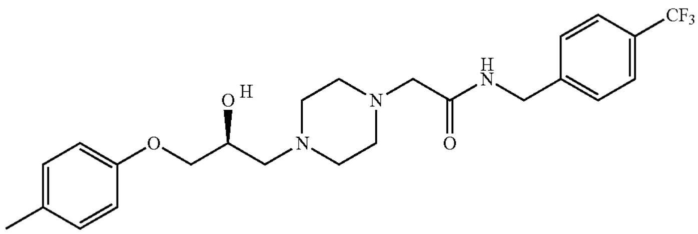 | 465.51 | | | 25.39 | 5 |
| KKRE10203 | 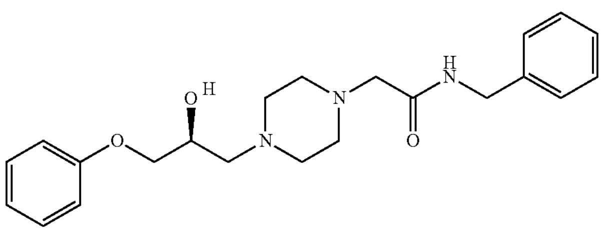 | 383.48 | | | 37.96 | 6 |
| KKRE10204 | 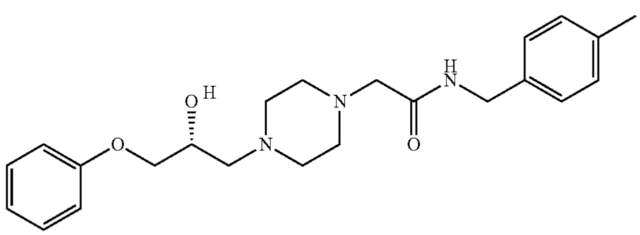 | 397.51 | | | 57.45 | 5 |
| KKRE10205 | 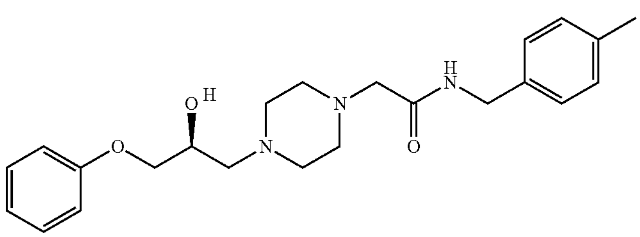 | 397.51 | | | 26.40 | 4 |
| KKRE10207 | 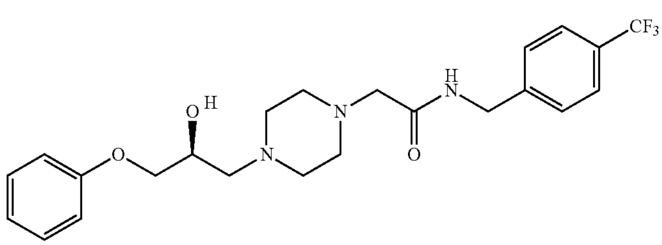 | 451.48 | | | 53.00 | 7 |

TABLE 3
| Name | Structure | M.W | block % at 100 μM | n | block % at 101 μM | n |
|---|---|---|---|---|---|---|
| quinine | | 324.42 | 50.00 ± 5.72 | 5 | 17.00 ± 6.93 | 5 |
| quinidine | | 324.42 | 33.46 ± 8.09 | 2 | | |
| hydroquinine | | 326.43 | 49.71 ± 5.83 | 5 | 19.84 ± 9.57 | 5 |
| KKRE10138 | 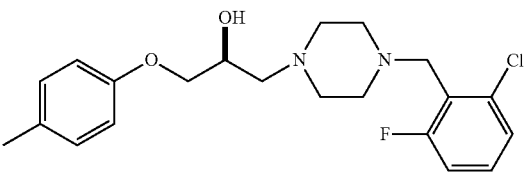 [SMILES: Cc1ccc(OC[C@@H](O)CN2CCN(Cc3c(F)cccc3Cl)CC2)cc1] | 392.89 | 71.47 ± 3.30 | 5 | 12.97 ± 10.11 | 4 |
| KKRE10145 | 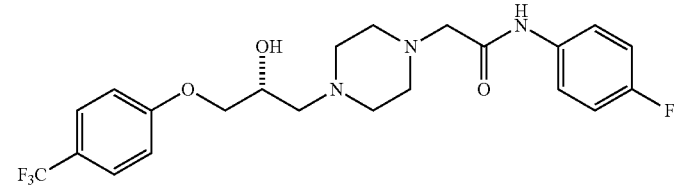 [SMILES: O=C(CN1CCN(C[C@@H](O)COc2ccc(C(F)(F)F)cc2)CC1)Nc1ccc(F)cc1] | 455.45 | | | 35.24 ± 4.89 | 5 |
| KKRE10153 | 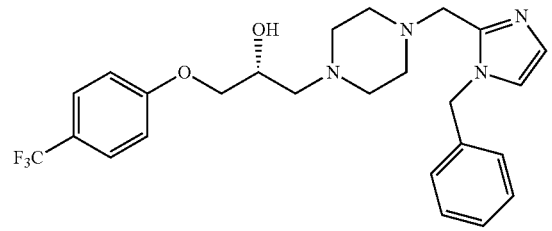 [SMILES: O[C@@H](COc1ccc(C(F)(F)F)cc1)CN1CCN(Cc2nccn2Cc2ccccc2)CC1] | 474.52 | | | 52.07 ± 7.24 | 5 |
| KKRE10162 | 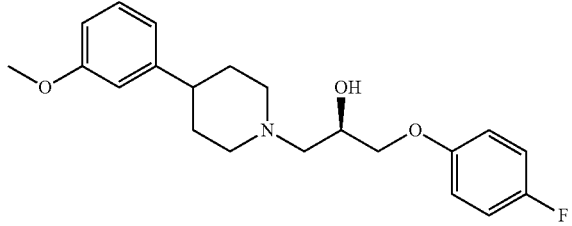 [SMILES: COc1cccc(C2CCN(C[C@@H](O)COc3ccc(F)cc3)CC2)c1] | 359.43 | | | 52.52 ± 6.76 | 6 |
| KKRE10174 | 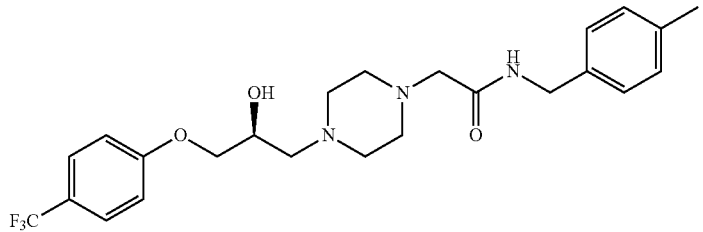 [SMILES: Cc1ccc(CNC(=O)CN2CCN(C[C@H](O)COc3ccc(C(F)(F)F)cc3)CC2)cc1] | 519.48 | 88.17 ± 4.60 | 6 | 37.63 ± 5.55 | 5 |
| KKRE10175 | 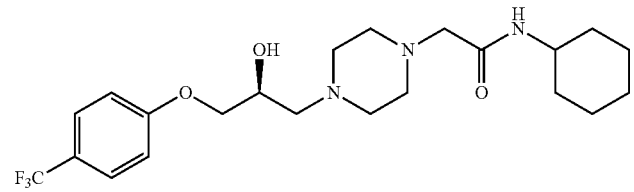 [SMILES: O=C(CN1CCN(C[C@H](O)COc2ccc(C(F)(F)F)cc2)CC1)NC1CCCCC1] | 465.51 | 74.61 ± 2.15 | 5 | 18.10 ± 6.92 | 4 |

TABLE 3-continued

| Name | Structure | M.W | block % at 100 μM | n | block % at 101 μM | n |
|---|---|---|---|---|---|---|
| KKRE10210 | 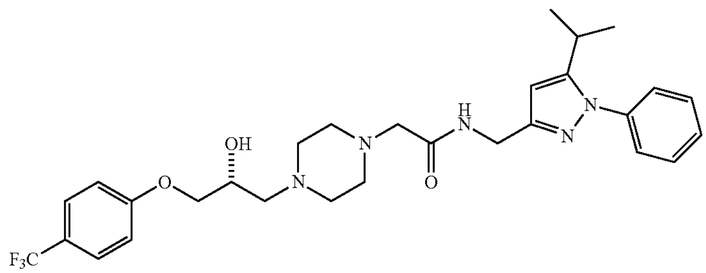 [SMILES: CC(C)c1cc(CNC(=O)CN2CCN(C[C@@H](O)COc3ccc(C(F)(F)F)cc3)CC2)nn1-c1ccccc1] | 573.65 | 91.22 ± 1.77 | 5 | 77.55 ± 5.19 | |
| KKRE10213 | (2HCl) | 596.56 | | | 64.67 ± 5.79 | 4 |
| KKRE10173 | 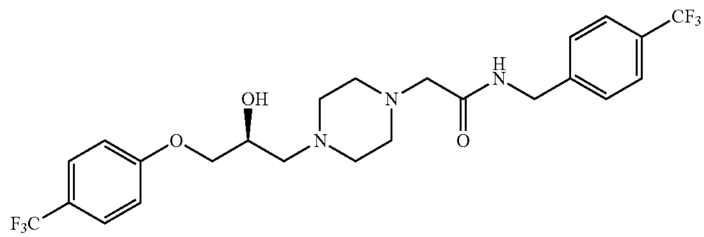 [SMILES: O=C(CN1CCN(C[C@H](O)COc2ccc(C(F)(F)F)cc2)CC1)NCc1ccc(C(F)(F)F)cc1] | 348.48 | | | 63.25 ± 7.60 | 5 |
| KKRE10174 | 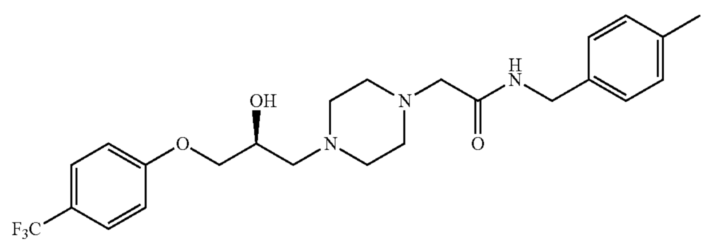 [SMILES: Cc1ccc(CNC(=O)CN2CCN(C[C@H](O)COc3ccc(C(F)(F)F)cc3)CC2)cc1] | 519.48 | | | 35.61 ± 5.66 | 7 |
| KKRE10196 | 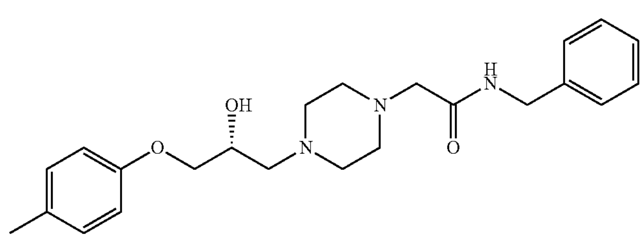 [SMILES: Cc1ccc(OC[C@H](O)CN2CCN(CC(=O)NCc3ccccc3)CC2)cc1] | 397.51 | | | 4.70 ± 1.04 | 5 |
| KKRE10197 | 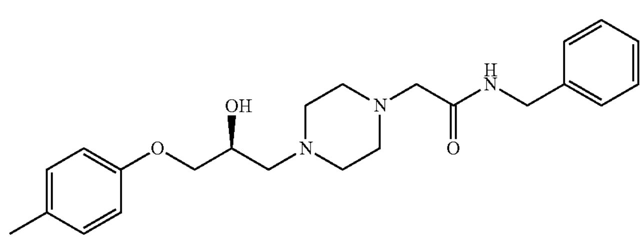 [SMILES: Cc1ccc(OC[C@@H](O)CN2CCN(CC(=O)NCc3ccccc3)CC2)cc1] | 397.51 | | | 13.50 ± 3.90 | 5 |

TABLE 3-continued

| Name | Structure | M.W | block % at 100 μM | n | block % at 101 μM | n |
|---|---|---|---|---|---|---|
| KKRE10198 | 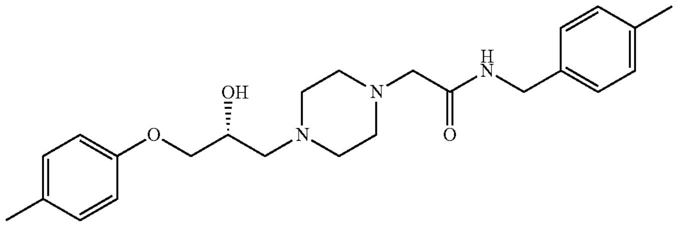 | 411.54 | | | 29.86 ± 3.90 | 5 |
| KKRE10199 | 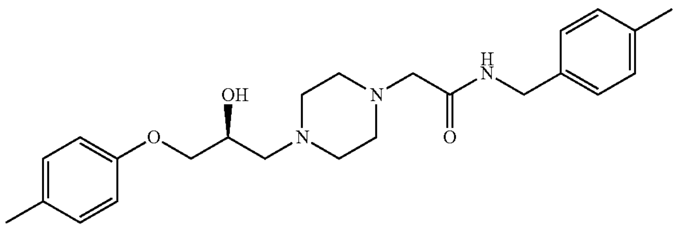 | 411.54 | | | 11.04 ± 2.58 | 5 |
| KKRE10200 | 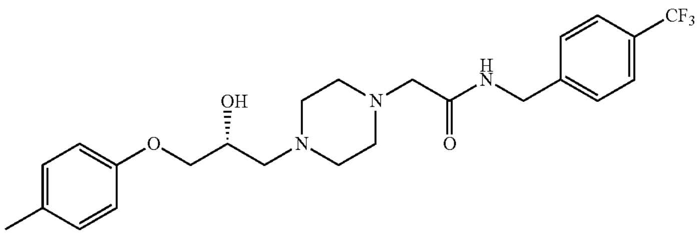 [SMILES: Cc1ccc(OC[C@H](O)CN2CCN(CC(=O)NCc3ccc(C(F)(F)F)cc3)CC2)cc1] | 465.51 | | | 30.94 ± 3.86 | 5 |
| KKRE10201 | 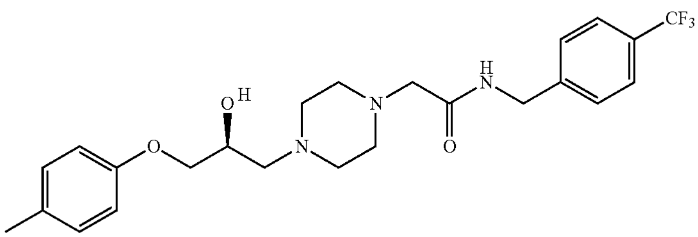 | 465.51 | | | 25.39 ± 7.87 | 5 |
| KKRE10202 | 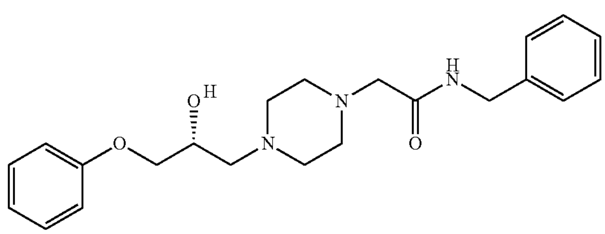 | 383.48 | | | 0.84 ± 1.76 | 5 |
| KKRE10203 | 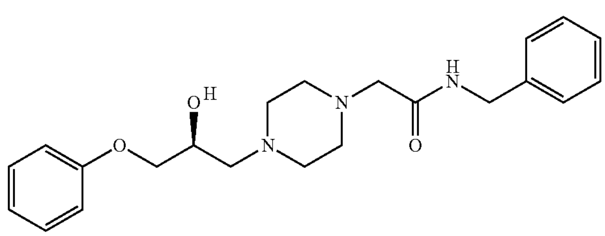 | 383.48 | | | 37.96 ± 6.42 | 6 |

TABLE 3-continued
| Name | Structure | M.W | block % at 100 μM | n | block % at 101 μM | n |
|---|---|---|---|---|---|---|
| KKRE10204 | 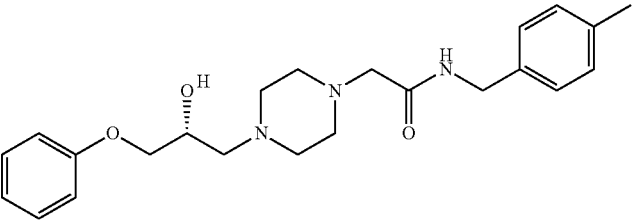 | 397.51 | | | 16.30 ± 12.87 | 5 |
| KKRE10205 | 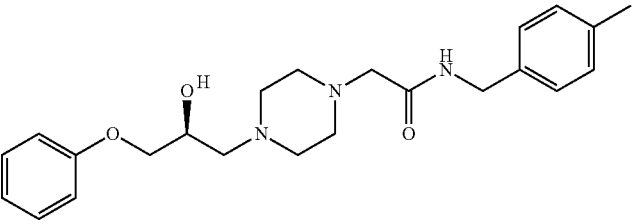 | 397.51 | | | 26.40 ± 12.19 | 4 |
| KKRE10207 | 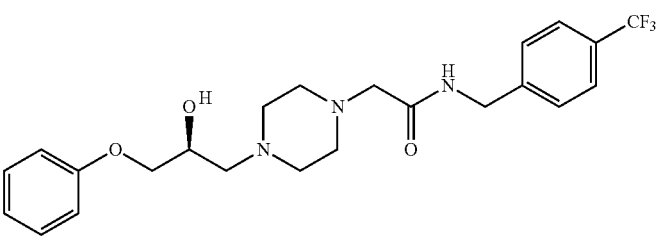 | 451.48 | | | 53.00 ± 5.98 | 7 |
| KKRE10154 | 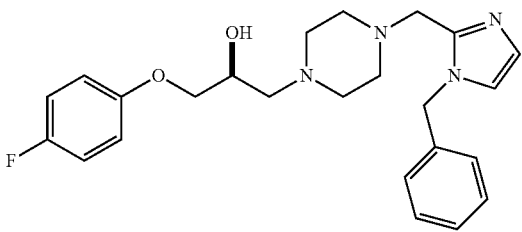 [SMILES: O[C@H](COc1ccc(F)cc1)CN1CCN(Cc2nccn2Cc2ccccc2)CC1] | 424.51 | | | 26.47 ± 3.97 | 6 |
| KKRE10155 | 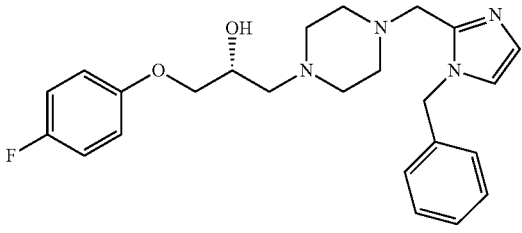 [SMILES: O[C@@H](COc1ccc(F)cc1)CN1CCN(Cc2nccn2Cc2ccccc2)CC1] | 424.51 | | | 23.99 ± 10.55 | 4 |
| KKRE10156 | 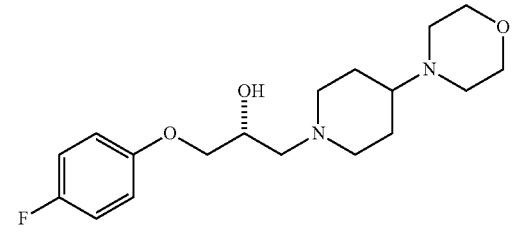 [SMILES: O[C@@H](COc1ccc(F)cc1)CN1CCC(N2CCOCC2)CC1] | 388.42 | | | 16.36 ± 5.65 | 6 |

TABLE 3-continued

| Name | Structure | M.W | block % at 100 μM | n | block % at 101 μM | n |
|---|---|---|---|---|---|---|
| KKRE10157 | 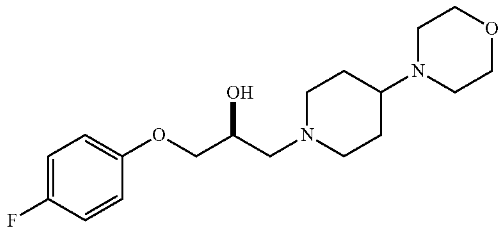 [SMILES: O[C@H](COc1ccc(F)cc1)CN1CCC(N2CCOCC2)CC1] | 388.42 | | | 29.59 ± 3.71 | 5 |
| KKRE10158 | 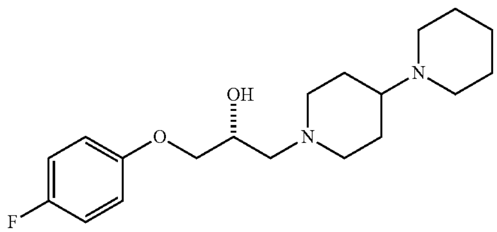 [SMILES: O[C@@H](COc1ccc(F)cc1)CN1CCC(N2CCCCC2)CC1] | 336.44 | | | 16.82 ± 2.73 | 5 |
| KKRE10159 | 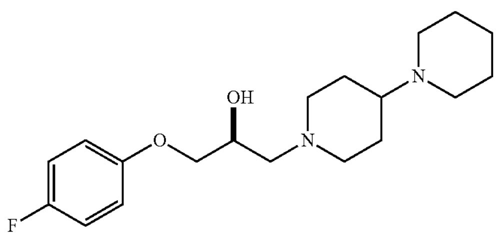 [SMILES: O[C@H](COc1ccc(F)cc1)CN1CCC(N2CCCCC2)CC1] | 336.44 | | | 13.37 ± 5.78 | 5 |
| KKRE10160 | 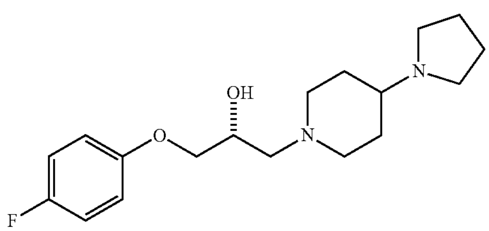 [SMILES: O[C@@H](COc1ccc(F)cc1)CN1CCC(N2CCCC2)CC1] | 322.42 | | | 4.13 ± 4.43 | 6 |
| KKRE10161 | 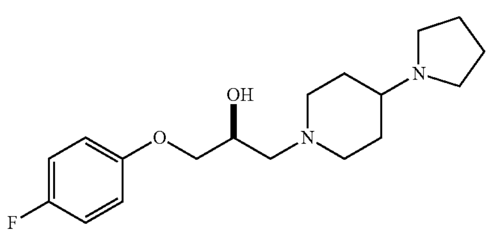 [SMILES: O[C@H](COc1ccc(F)cc1)CN1CCC(N2CCCC2)CC1] | 322.42 | | | 8.28 ± 3.49 | 5 |
| KKRE10176 | 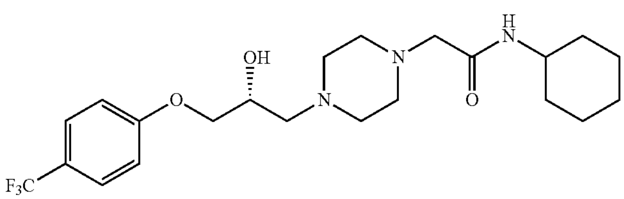 [SMILES: O=C(CN1CCN(C[C@@H](O)COc2ccc(C(F)(F)F)cc2)CC1)NC1CCCCC1] | 516.42 | | | 33.47 ± 5.67 | 6 |
| KKRE10177 | 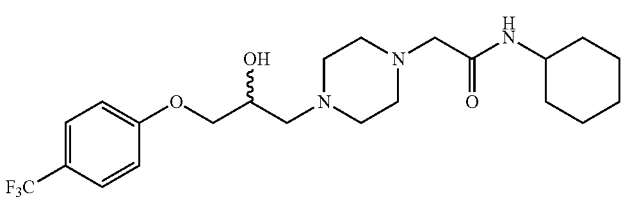 [SMILES: O=C(CN1CCN(CC(O)COc2ccc(C(F)(F)F)cc2)CC1)NC1CCCCC1] | 516.42 | | | 42.54. ± 7.53 | 6 |

TABLE 3-continued

| Name | Structure | M.W | block % at 100 μM | n | block % at 101 μM | n |
|---|---|---|---|---|---|---|
| KKRE10178 | 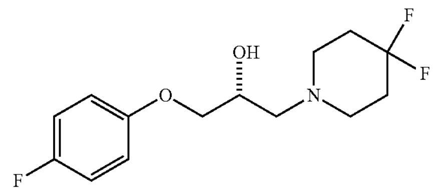 [SMILES: O[C@@H](COc1ccc(F)cc1)CN1CCC(F)(F)CC1] | 516.42 | | | 66.03 ± 4.05 | 7 |
| KKRE10179 | 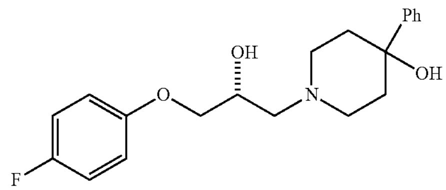 [SMILES: O[C@@H](COc1ccc(F)cc1)CN1CCC(O)(c2ccccc2)CC1] | 345.41 | | | 19.91 ± 4.25 | 6 |
| KKRE10180 | 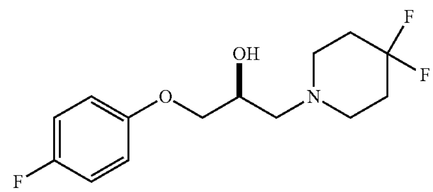 [SMILES: O[C@H](COc1ccc(F)cc1)CN1CCC(F)(F)CC1] | 516.42 | | | 23.29 ± 10.02 | 4 |
| KKRE10181 | 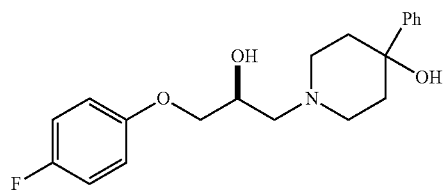 [SMILES: O[C@H](COc1ccc(F)cc1)CN1CCC(O)(c2ccccc2)CC1] | 345.41 | | | 53.87 ± 1.62 | 5 |
| KKRE10182 | 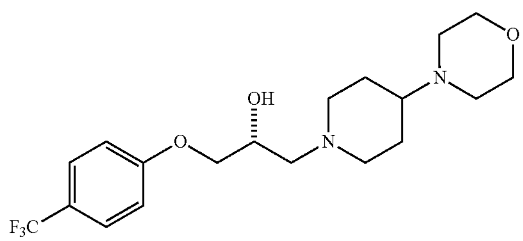 [SMILES: O[C@@H](COc1ccc(C(F)(F)F)cc1)CN1CCC(N2CCOCC2)CC1] | 388.42 | | | 46.64 ± 6.25 | 5 |
| KKRE10183 | 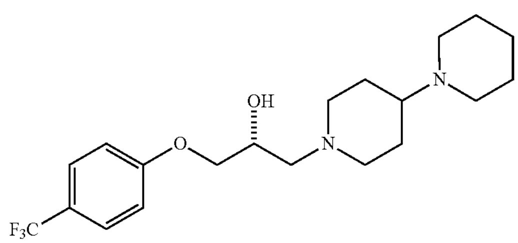 [SMILES: O[C@@H](COc1ccc(C(F)(F)F)cc1)CN1CCC(N2CCCCC2)CC1] | 386.45 | | | 36.36 ± 7.38 증가 | 4 |
| KKRE10184 | 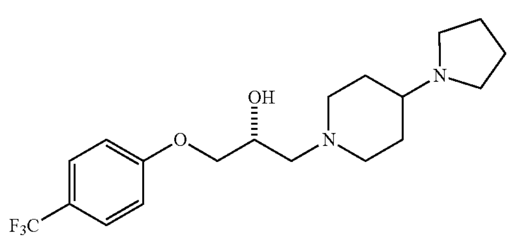 [SMILES: O[C@@H](COc1ccc(C(F)(F)F)cc1)CN1CCC(N2CCCC2)CC1] | 372.43 | | | 37.37 ± 6.98 | 5 |

TABLE 3-continued

| Name | Structure | M.W | block % at 100 μM | n | block % at 101 μM | n |
|---|---|---|---|---|---|---|
| KKRE10185 | 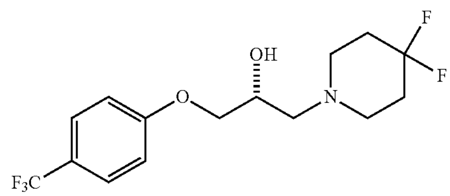 [SMILES: O[C@@H](COc1ccc(C(F)(F)F)cc1)CN1CCC(F)(F)CC1] | 339.3 | | | 60.77 ± 7.47 | 5 |
| KKRE10186 | 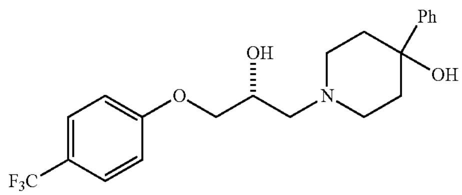 [SMILES: O[C@@H](COc1ccc(C(F)(F)F)cc1)CN1CCC(O)(c2ccccc2)CC1] | 395.42 | | | 54 ± 12.11 | 4 |
| KKRE10187 | 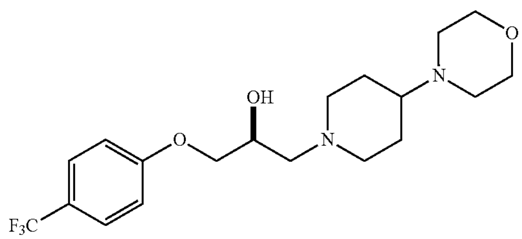 [SMILES: O[C@H](COc1ccc(C(F)(F)F)cc1)CN1CCC(N2CCOCC2)CC1] | 388.42 | | | 49.18 ± 6.75 | 5 |
| KKRE10188 | 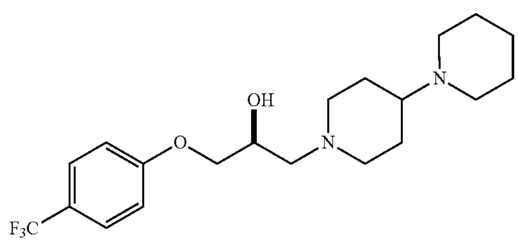 [SMILES: O[C@H](COc1ccc(C(F)(F)F)cc1)CN1CCC(N2CCCCC2)CC1] | 386.45 | | | 55.6 ± .23 | 5 |
| KKRE10189 | 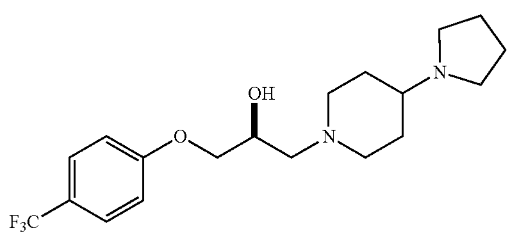 [SMILES: O[C@H](COc1ccc(C(F)(F)F)cc1)CN1CCC(N2CCCC2)CC1] | 372.43 | | | 75.44.± 4.72 | 4 |
| KKRE10190 | 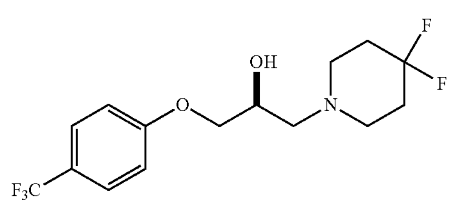 [SMILES: O[C@H](COc1ccc(C(F)(F)F)cc1)CN1CCC(F)(F)CC1] | 339.3 | | | 7.42.± 5.32 | 5 |
| KKRE10206 | 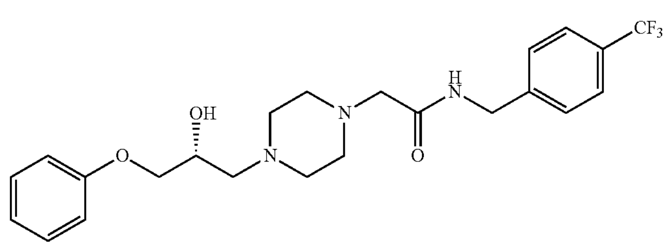 [SMILES: O=C(CN1CCN(C[C@@H](O)COc2ccccc2)CC1)NCc1ccc(C(F)(F)F)cc1] | 451.48 | | | 43.96 ± 7.7 | 5 |

TABLE 3-continued
| Name | Structure | M.W | block % at 100 μM | n | block % at 101 μM | n |
|---|---|---|---|---|---|---|
| KKRE10211 | 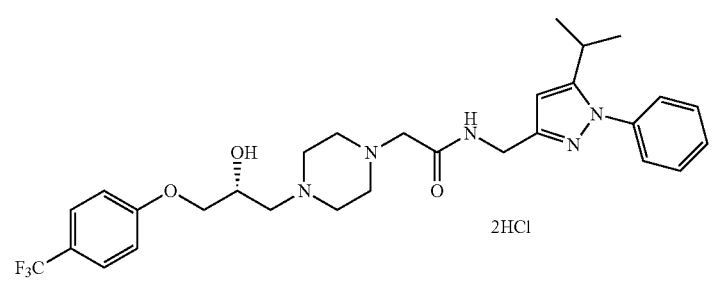 2HCl | 632.54 | | | 55.29 ± 6.53 | 5 |
| KKRE10213 | 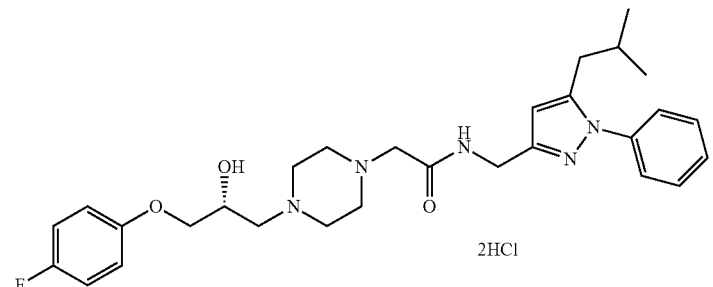 2HCl | 596.56 | | | 39.41 ± 3.58 | 5 |
| KKRE10214 | 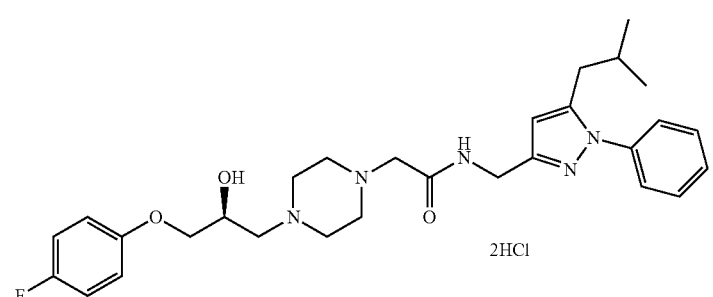 2HCl | 596.56 | | | 37.47 ± 5.31 | 5 |
| KKRE10215 | 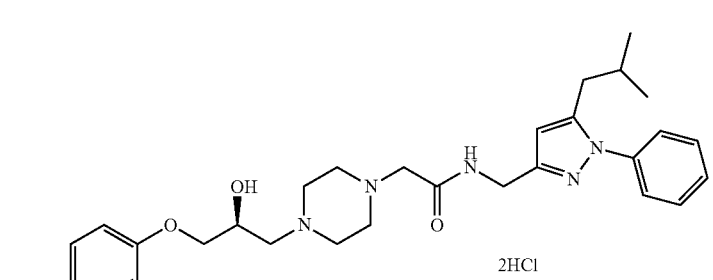 2HCl | 646.57 | | | 82.07 ± 3.81 | 5 |
| KKRE10216 | 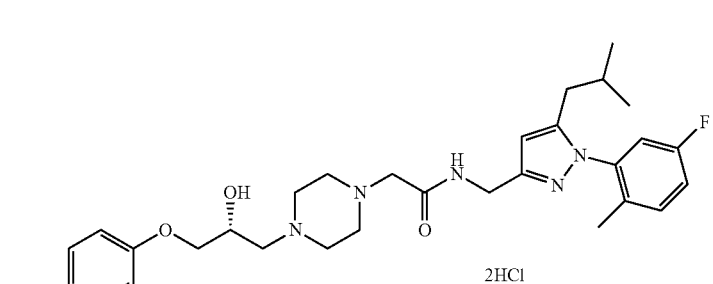 2HCl | 678.59 | | | 71.36 ± 10.83 | 5 |

TABLE 3-continued

| Name | Structure | M.W | block % at 100 μM | n | block % at 101 μM | n |
|---|---|---|---|---|---|---|
| KKRE10217 | (structure) 2HCl | 664.56 | | | 50.08 ± 10.69 | 5 |
| KKRE10218 | (structure) 2HCl | 715.46 | | | 76.14 ± 5.79 | 5 |
| KKRE10219 | (structure) 2HCl | 664.56 | | | 56.97 ± 6.08 | 5 |
| KKRE10220 | (structure) | 642.54 | | | 41.43 ± 12.73 | 5 |
| KKRE10221 | (structure) | 605.67 | | | 83.12 ± 4.99 | 5 |

TABLE 3-continued

| Name | Structure | M.W | block % at 100 μM | n | block % at 101 μM | n |
|---|---|---|---|---|---|---|
| KKRE10222 | 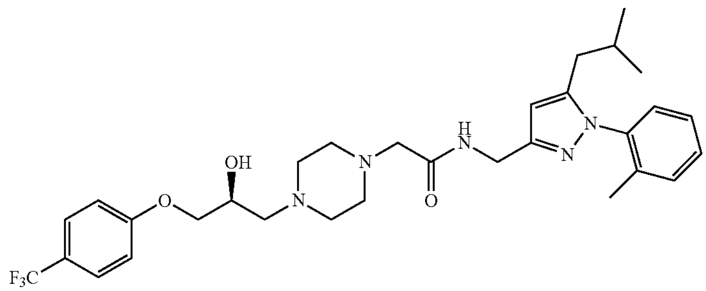 [SMILES: Cc1ccccc1-n1nc(CNC(=O)CN2CCN(C[C@H](O)COc3ccc(C(F)(F)F)cc3)CC2)cc1CC(C)C] | 587.68 | | | 51.25 ± 12.46 | 7 |
| KKRE10223 | 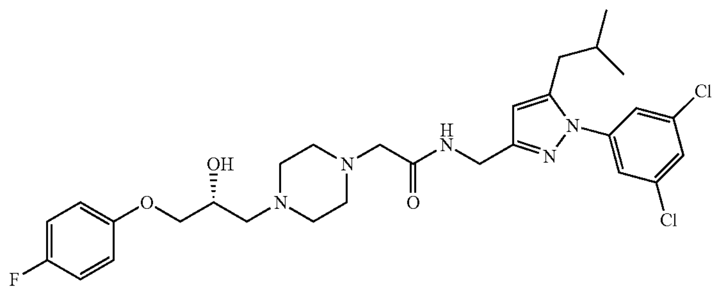 [SMILES: CC(C)Cc1cc(CNC(=O)CN2CCN(C[C@@H](O)COc3ccc(F)cc3)CC2)nn1-c1cc(Cl)cc(Cl)c1] | 592.53 | | | 87.64 ± 2.43 | 5 |
| KKRE10224 | 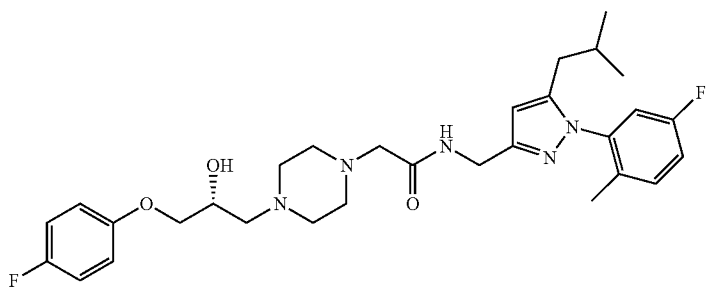 [SMILES: Cc1ccc(F)cc1-n1nc(CNC(=O)CN2CCN(C[C@@H](O)COc3ccc(F)cc3)CC2)cc1CC(C)C] | 555.66 | | | 45.11 ± 3.6 | 5 |
| KKRE10225 | 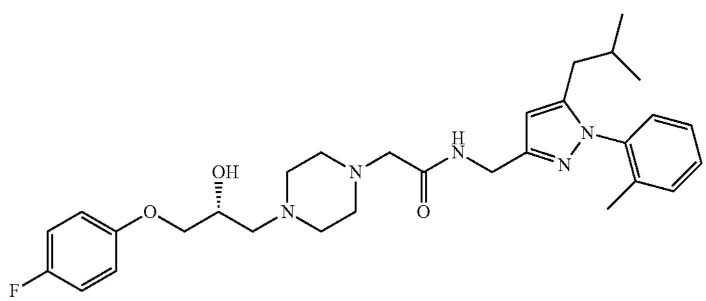 [SMILES: Cc1ccccc1-n1nc(CNC(=O)CN2CCN(C[C@@H](O)COc3ccc(F)cc3)CC2)cc1CC(C)C] | 537.67 | | | 13.05 ± 6.19 | 5 |
| KKRE10226 | 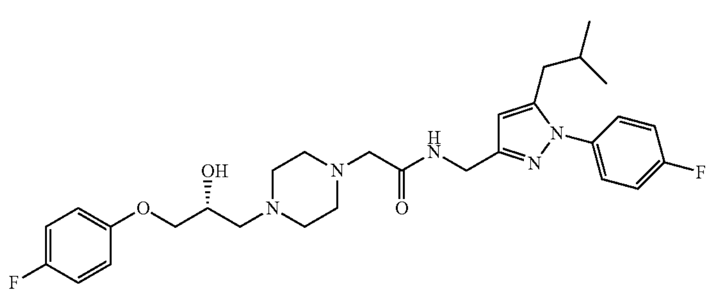 [SMILES: CC(C)Cc1cc(CNC(=O)CN2CCN(C[C@@H](O)COc3ccc(F)cc3)CC2)nn1-c1ccc(F)cc1] | 541.63 | | | 18.79 ± 7.78 | 5 |

TABLE 3-continued

| Name | Structure | M.W | block % at 100 μM | n | block % at 101 μM | n |
|---|---|---|---|---|---|---|
| KKRE10227 | 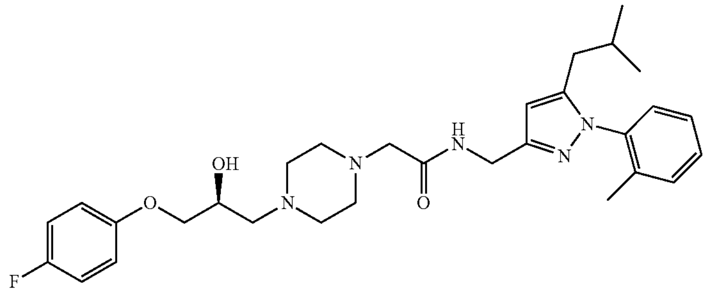 [SMILES: Cc1ccccc1-n1nc(CNC(=O)CN2CCN(C[C@H](O)COc3ccc(F)cc3)CC2)cc1CC(C)C] | 537.67 | | | 69.77 ± 4.78 | 5 |
| KKRE10228 | 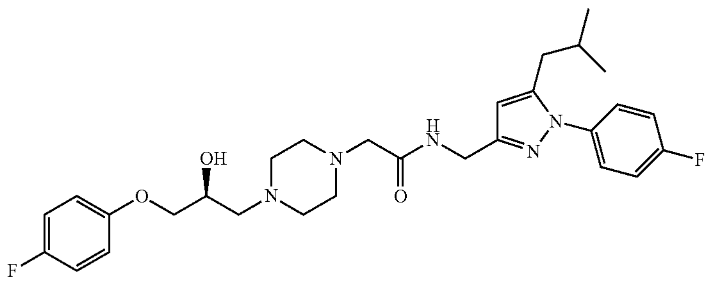 [SMILES: CC(C)Cc1cc(CNC(=O)CN2CCN(C[C@H](O)COc3ccc(F)cc3)CC2)nn1-c1ccc(F)cc1] | 541.63 | | | 58.61 ± 4.35 | 5 |
| KKRE10229 | 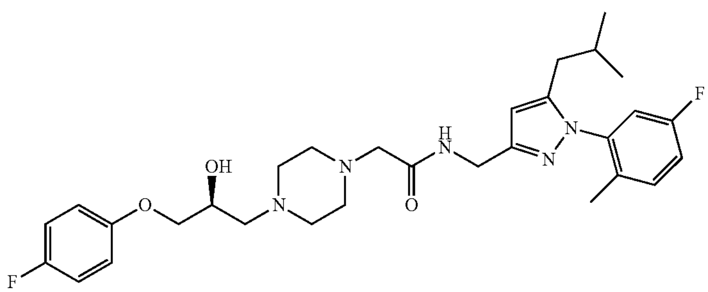 [SMILES: Cc1ccc(F)cc1-n1nc(CNC(=O)CN2CCN(C[C@H](O)COc3ccc(F)cc3)CC2)cc1CC(C)C] | 555.66 | | | 74.13 ± 2.75 | 5 |
| KKRE10230 | 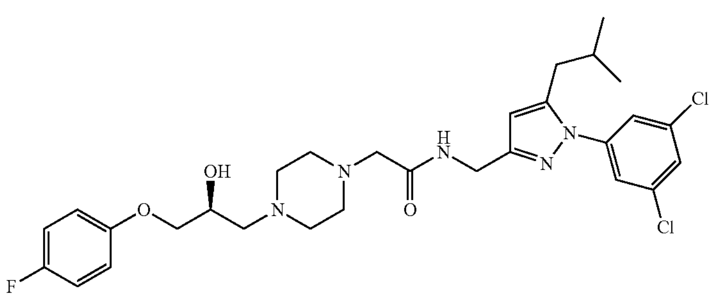 [SMILES: CC(C)Cc1cc(CNC(=O)CN2CCN(C[C@H](O)COc3ccc(F)cc3)CC2)nn1-c1cc(Cl)cc(Cl)c1] | 592.53 | | | 78.12 ± 2.95 | 5 |

TABLE 3-continued

| Name | Structure | M.W | block % at 100 μM | n | block % at 101 μM | n |
|---|---|---|---|---|---|---|
| KKRE10231 | 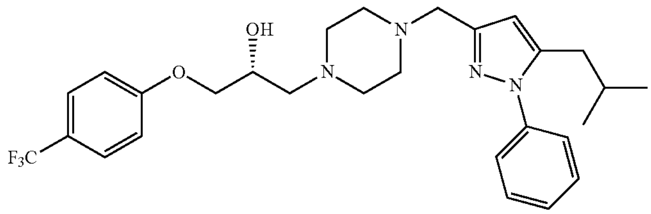 [SMILES: CC(C)Cc1cc(CN2CCN(C[C@@H](O)COc3ccc(C(F)(F)F)cc3)CC2)nn1-c1ccccc1] | 516.6 | | | 48.5 ± 4.26 | 5 |
| KKRE10232 | 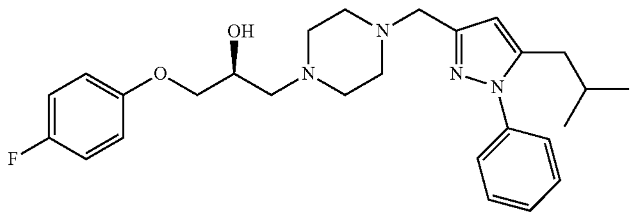 [SMILES: CC(C)Cc1cc(CN2CCN(C[C@H](O)COc3ccc(F)cc3)CC2)nn1-c1ccccc1] | 466.59 | | | 21.7 ± 3.13 | 5 |
| KKRE10233 | 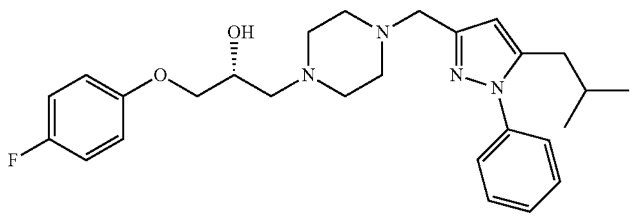 [SMILES: CC(C)Cc1cc(CN2CCN(C[C@@H](O)COc3ccc(F)cc3)CC2)nn1-c1ccccc1] | 466.59 | | | 21.59 ± 4.63 | 4 |
| KKRE10234 | 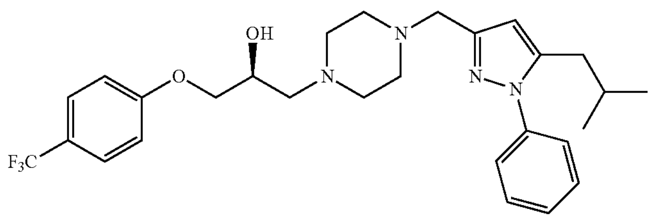 [SMILES: CC(C)Cc1cc(CN2CCN(C[C@H](O)COc3ccc(C(F)(F)F)cc3)CC2)nn1-c1ccccc1] | 516.6 | | | 84.19 ± 2.22 | 8 |

What is claimed is:

1. A phenoxypropanol derivative having the structure of Chemical Formula I, and a racemate thereof, a pharmaceutically acceptable salt thereof, a solvate thereof and a hydrate thereof,

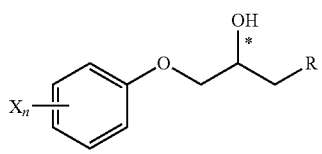

[Chemical Formula I]

wherein * represents an (R)-form or an (S)-form,

X is selected from the group consisting of hydrogen, halogen, and substituted or unsubstituted straight or branched alkyl having 1 to 4 carbon atoms, and n represents the number of X and is an integer of 1 to 5, wherein at least a hydrogen is replaced with halogen in the substituted linear or branched alkyl having 1 to 4 carbon atoms, R is selected from compounds of the following Chemical Formulae IV,

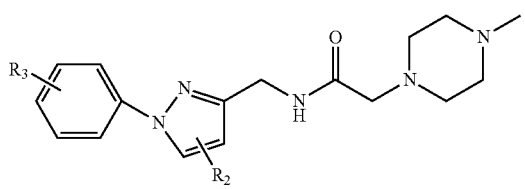

[Chemical Formula IV]

wherein: R2 may be each independently selected from the group consisting of straight or branched alkyl having 1 to 4 carbon atoms and cycloalkyl having 3 to 8 carbon atoms, and one or two thereof may exist, R3 is a substituent binding to carbon of the phenyl group, and one or two thereof may exist, and may be each independently one or more selected from the group consisting of hydrogen, straight or branched alkyl having 1 to 4 carbon atoms, straight or branched alkyl having 1 to 4 carbon atoms, of which one or more hydrogens are substituted with halogen.

2. The phenoxypropanol derivative, a racemate thereof, a pharmaceutically acceptable salt thereof, a solvate thereof and a hydrate thereof according to claim 1, wherein
the substituent X is selected from the group consisting of hydrogen, methyl and trifluoromethyl, the substituent R2 is selected from the group consisting of isobutyl, isopropyl and cyclopropyl, the substituent R3 is selected from the group consisting of methyl, trifluoromethyl and halogen.

3. The phenoxypropanol derivative, a racemate thereof, a pharmaceutically acceptable salt thereof, a solvate thereof and a hydrate thereof according to claim 1, wherein the phenoxypropanol derivative may be selected from the group consisting of the following compounds.

(R)-2-(4-(2-hydroxy-3-(4-(trifluoromethyl)phenoxy)propyl)piperazin-1-yl)-N-((5-isobutyl-1-phenyl-1H-pyrazol-3-yl)methyl)acetamide;

(R)-2-(4-(2-hydroxy-3-(4-(trifluoromethyl)phenoxy)propyl)piperazin-1-yl)-N-((5-isopropyl-1-phenyl-1H-pyrazol-3-yl)methyl)acetamide;

(R)-N-((5-cyclopropyl-1-phenyl-1H-pyrazol-3-yl)methyl)-2-(4-(2-hydroxy-3-(4-(trifluoromethyl)phenoxy)propyl)piperazin-1-yl)acetamide;

(R)-2-(4-(3-(4-fluorophenoxy)-2-hydroxypropyl)piperazin-1-yl)-N-((5-isobutyl-1-phenyl-1H-pyrazol-3-yl)methyl)acetamide;

(S)-2-(4-(3-(4-fluorophenoxy)-2-hydroxypropyl)piperazin-1-yl)-N-((5-isobutyl-1-phenyl-1H-pyrazol-3-yl)methyl)acetamide;

(S)-2-(4-(2-hydroxy-3-(4-(trifluoromethyl)phenoxy)propyl)piperazin-1-yl)-N-((5-isobutyl-1-phenyl-1H-pyrazol-3-yl)methyl)acetamide;

(R)-N-((1-(5-fluoro-2-methylphenyl)-5-isobutyl-1H-pyrazol-3-yl)methyl)-2-(4-(2-hydroxy-3-(4-(trifluoromethyl)phenoxy)propyl)piperazin-1-yl)acetamide;

(R)-N-((1-(4-fluoromethyl)-5-isobutyl-1H-pyrazol-3-yl)methyl)-2-(4-(2-hydroxy-3-(4-(trifluoromethyl)phenoxy)propyl)piperazin-1-yl)acetamide;

(R)-N-((1-(3,5-dichlorophenyl)-5-isobutyl-1H-pyrazol-3-yl)methyl)-2-(4-(2-hydroxy-3-(4-(trifluoromethyl)phenoxy)propyl)piperazin-1-yl)acetamide;

(S)-N-((1-(4-fluorophenyl)-5-isobutyl-1H-pyrazol-3-yl)methyl)-2-(4-(2-hydroxy-3-(4-(trifluoromethyl)phenoxy)propyl)piperazin-1-yl)acetamide;

(S)-N-((1-(3,5-dichlorophenyl)-5-isobutyl-1H-pyrazol-3-yl)methyl)-2-(4-(2-hydroxy-3-(4-(trifluoromethyl)phenoxy)propyl)piperazin-1-yl)acetamide;

(S)-N-((1-(5-fluoro-2-methylphenyl)-5-isobutyl-1H-pyrazol-3-yl)methyl)-2-(4-(2-hydroxy-3-(4-(trifluoromethyl)phenoxy)propyl)piperazin-1-yl)acetamide;

(S)-2-(4-(2-hydroxy-3-(4-(trifluoromethyl)phenoxy)propyl)piperazin-1-yl)-N-((5-isobutyl-1-o-tolyl-1H-pyrazol-3-yl)methyl)acetamide;

(R)-N-((1-(3,5-dichlorophenyl)-5-isobutyl-1H-pyrazol-3-yl)methyl)-2-(4-(3-(4-fluorophenoxy)-2-hydroxypropyl)piperazin-1-yl)acetamide;

(R)-N-((1-(5-fluoro-2-methylphenyl)-5-isobutyl-1H-pyrazol-3-yl)methyl)-2-(4-(3-(4-fluorophenoxy)-2-hydroxypropyl)piperazin-1-yl)acetamide;

(R)-2-(4-(3-(4-fluorophenoxy)-2-hydroxypropyl)piperazin-1-yl)-N-((5-isobutyl-1-o-tolyl-1H-pyrazol-3-yl)methyl)acetamide;

(R)-2-(4-(3-(4-fluorophenoxy)-2-hydroxypropyl)piperazin-1-yl)-N-((1-(4-fluorophenyl)-5-isobutyl-1H-pyrazol-3-yl)methyl)acetamide;

(S)-2-(4-(3-(4-fluorophenoxy)-2-hydroxypropyl)piperazin-1-yl)-N-((5-isobutyl-1-o-tolyl-1H-pyrazol-3-yl)methyl)acetamide;

(S)-2-(4-(3-(4-fluorophenoxy)-2-hydroxypropyl)piperazin-1-yl)-N-((1-(4-fluorophenyl)-5-isobutyl-1H-pyrazol-3-yl)methyl)acetamide;

(S)-N-((1-(5-fluoro-2-methylphenyl)-5-isobutyl-1H-pyrazol-3-yl)methyl)-2-(4-(3-(4-fluorophenoxy)-2-hydroxypropyl)piperazin-1-yl)acetamide; and (S)-N-((1-(3,5-dichlorophenyl)-5-isobutyl-1H-pyrazol-3-yl)methyl)-2-(4-(3-(4-fluorophenoxy)-2-hydroxypropyl)piperazin-1-yl)acetamide.

* * * * *